(12) United States Patent
Wright et al.

(10) Patent No.: US 11,389,345 B2
(45) Date of Patent: *Jul. 19, 2022

(54) METHOD OF MAKING AN ABSORBENT COMPOSITE

(71) Applicant: DSG TECHNOLOGY HOLDINGS LTD, Kwai Chung (HK)

(72) Inventors: Andrew C. Wright, Derbyshire (GB); Eugenio Varona, Marietta, GA (US); Anne Smid, Wolvega (NL); Dennis Smid, Wolvega (NL)

(73) Assignee: DSG Technology Holdings Ltd., Kwai Chung (HK)

( * ) Notice: Subject to any disclaimer, the term of this patent is extended or adjusted under 35 U.S.C. 154(b) by 931 days.

This patent is subject to a terminal disclaimer.

(21) Appl. No.: 15/669,714

(22) Filed: Aug. 4, 2017

(65) Prior Publication Data
US 2018/0014985 A1   Jan. 18, 2018

Related U.S. Application Data

(63) Continuation of application No. 14/214,868, filed on Mar. 15, 2014, now Pat. No. 9,789,014, which is a
(Continued)

(51) Int. Cl.
*A61F 13/539* (2006.01)
*A61F 13/15* (2006.01)
(Continued)

(52) U.S. Cl.
CPC ...... *A61F 13/539* (2013.01); *A61F 13/15658* (2013.01); *A61F 13/15699* (2013.01);
(Continued)

(58) Field of Classification Search
None
See application file for complete search history.

(56) References Cited

U.S. PATENT DOCUMENTS

| | | |
|---|---|---|
| 3,071,138 A | 1/1963 | Gustavo |
| 3,670,731 A | 6/1972 | Harmon |

(Continued)

FOREIGN PATENT DOCUMENTS

| | | |
|---|---|---|
| CN | 1177472 A | 4/1998 |
| CN | 101426461 A | 5/2009 |

(Continued)

OTHER PUBLICATIONS

Extended EP Search Report, issued in EP Application No. 20156193.3 dated Aug. 21, 2020 [12 pages].
(Continued)

*Primary Examiner* — Barbara J Musser
(74) *Attorney, Agent, or Firm* — Alberto Q. Amatong, Jr.; Amatong McCoy LLC

(57) ABSTRACT

Disclosed is an absorbent core composite for a disposable absorbent article. The absorbent composite has a first fabric, a body side second fabric, and a plurality of aggregates of superabsorbent particles (SAP) situated between the first fabric second fabric. About each of a plurality of the SAP aggregates, an arrangement of spaced apart bond sites secure the second fabric to the first fabric and form a pocket in which the SAP aggregate is secured between the first fabric and the second fabric. The body side second fabric is a bulky nonwoven including fibers that entangle at least some particles in the SAP aggregate.

21 Claims, 22 Drawing Sheets

Related U.S. Application Data continuation-in-part of application No. 14/026,927, filed on Sep. 13, 2013, now Pat. No. 9,566,198.

(60) Provisional application No. 61/801,620, filed on Mar. 15, 2013.

(51) Int. Cl.

| | | |
|---|---|---|
| *A61F 13/53* | (2006.01) | |
| *A61F 13/534* | (2006.01) | |
| *A61F 13/536* | (2006.01) | |
| *A61F 13/535* | (2006.01) | |
| *A61F 13/532* | (2006.01) | |

(52) U.S. Cl.
CPC .......... *A61F 13/534* (2013.01); *A61F 13/535* (2013.01); *A61F 13/536* (2013.01); *A61F 13/5323* (2013.01); *A61F 13/5395* (2013.01); *A61F 2013/530481* (2013.01); *A61F 2013/530598* (2013.01); *A61F 2013/53908* (2013.01); *Y10T 156/10* (2015.01); *Y10T 156/1039* (2015.01)

(56) References Cited

U.S. PATENT DOCUMENTS

| | | |
|---|---|---|
| 3,780,399 A | 12/1973 | Morel |
| 3,814,100 A | 6/1974 | Nystrand et al. |
| 4,055,180 A | 10/1977 | Karami |
| 4,100,324 A | 7/1978 | Anderson et al. |
| 4,360,021 A | 11/1982 | Stima |
| 4,381,783 A | 5/1983 | Elias |
| 4,434,010 A | 2/1984 | Ash |
| 4,646,362 A | 3/1987 | Heran et al. |
| 4,670,011 A | 6/1987 | Mesek |
| 4,673,402 A | 6/1987 | Weisman et al. |
| 4,715,918 A | 12/1987 | Lang |
| 4,820,577 A | 4/1989 | Morman et al. |
| 4,960,477 A | 10/1990 | Mesek |
| 5,008,143 A | 4/1991 | Armanini |
| 5,037,412 A | 8/1991 | Tanzer et al. |
| 5,098,423 A | 3/1992 | Pieniak et al. |
| 5,122,407 A | 6/1992 | Yeo et al. |
| 5,149,335 A | 9/1992 | Kellenberger et al. |
| 5,281,207 A | 1/1994 | Chmielewski et al. |
| 5,294,478 A | 3/1994 | Wanek et al. |
| 5,336,552 A | 8/1994 | Strack et al. |
| 5,342,333 A | 8/1994 | Tanzer et al. |
| 5,350,370 A | 9/1994 | Jackson et al. |
| 5,364,380 A | 11/1994 | Tanzer et al. |
| 5,411,497 A | 5/1995 | Tanzer et al. |
| 5,425,725 A | 6/1995 | Tanzer et al. |
| 5,433,715 A | 7/1995 | Tanzer et al. |
| 5,436,066 A | 7/1995 | Chen |
| 5,448,464 A | 9/1995 | Moss et al. |
| 5,458,592 A | 10/1995 | Abuto et al. |
| 5,482,761 A * | 1/1996 | Palumbo .......... B32B 5/26 264/126 |
| 5,494,622 A | 2/1996 | Heath et al. |
| 5,505,718 A | 4/1996 | Roe et al. |
| H1565 H | 7/1996 | Brodof et al. |
| H1585 H | 8/1996 | Ahr |
| 5,549,589 A | 8/1996 | Horney et al. |
| 5,562,645 A | 10/1996 | Tanzer et al. |
| 5,562,646 A | 10/1996 | Goldman et al. |
| 5,567,744 A | 10/1996 | Nagata et al. |
| 5,591,149 A | 1/1997 | Cree et al. |
| 5,593,399 A | 1/1997 | Tanzer et al. |
| 5,599,335 A | 2/1997 | Goldman et al. |
| 5,601,542 A | 2/1997 | Melius et al. |
| 5,650,222 A | 7/1997 | DesMarais et al. |
| 5,653,702 A | 8/1997 | Brohammer et al. |
| 5,669,894 A | 9/1997 | Goldman et al. |
| 5,695,486 A | 12/1997 | Broughton et al. |
| 5,749,259 A | 5/1998 | Hamouda et al. |
| 5,763,331 A | 6/1998 | Demhartner |
| 5,782,819 A | 7/1998 | Tanzer et al. |
| 5,788,684 A | 8/1998 | Abuto et al. |
| 5,800,418 A | 9/1998 | Ahr |
| 5,821,179 A | 10/1998 | Masaki et al. |
| 5,853,403 A | 12/1998 | Tanzer et al. |
| 5,863,288 A | 1/1999 | Baker |
| 5,925,439 A | 7/1999 | Haubach |
| 5,938,650 A | 8/1999 | Baer et al. |
| 5,941,862 A | 8/1999 | Haynes et al. |
| 5,944,706 A | 8/1999 | Palumbo et al. |
| 5,947,947 A | 9/1999 | Tanzer et al. |
| 5,994,614 A | 11/1999 | Wada et al. |
| 6,024,822 A | 2/2000 | Alper et al. |
| 6,046,377 A | 4/2000 | Huntoon et al. |
| 6,068,620 A | 5/2000 | Chmielewski |
| 6,071,549 A | 6/2000 | Hansen |
| 6,086,950 A * | 7/2000 | Masaki ................... D21H 21/22 427/180 |
| 6,093,474 A | 7/2000 | Sironi |
| 6,129,720 A | 10/2000 | Blenke et al. |
| 6,140,550 A | 10/2000 | Beihoffer et al. |
| 6,152,906 A | 11/2000 | Faulks et al. |
| 6,162,959 A | 12/2000 | O'Connor |
| 6,177,607 B1 | 1/2001 | Blaney et al. |
| 6,238,379 B1 | 5/2001 | Keuhn et al. |
| H1969 H | 6/2001 | Fell et al. |
| 6,241,713 B1 | 6/2001 | Gross et al. |
| 6,245,693 B1 | 6/2001 | Gagliardi et al. |
| 6,258,076 B1 | 7/2001 | Glaug et al. |
| H1978 H | 8/2001 | Freiburger et al. |
| 6,290,686 B1 | 9/2001 | Tanzer |
| 6,329,565 B1 | 12/2001 | Dutkiewicz et al. |
| 6,368,990 B1 | 4/2002 | Jennergren et al. |
| 6,392,116 B1 | 5/2002 | Beihoffer et al. |
| 6,420,626 B1 | 7/2002 | Erspamer et al. |
| 6,429,350 B1 | 8/2002 | Tanzer et al. |
| 6,458,877 B1 | 10/2002 | Ahmed et al. |
| 6,491,677 B1 | 12/2002 | Glaug et al. |
| 6,500,251 B1 | 12/2002 | Andes et al. |
| 6,534,572 B1 | 3/2003 | Ahmed et al. |
| 6,548,732 B2 | 4/2003 | Erdman et al. |
| 6,569,137 B2 | 5/2003 | Suzuki et al. |
| 6,570,056 B1 | 5/2003 | Tanzer et al. |
| 6,592,960 B1 | 7/2003 | Suzuki et al. |
| 6,610,900 B1 | 8/2003 | Tanzer |
| 6,632,209 B1 | 10/2003 | Chmielewski |
| 6,645,407 B2 | 11/2003 | Kellenberger et al. |
| 6,677,498 B2 | 1/2004 | Chen et al. |
| 6,680,423 B1 | 1/2004 | Tanzer |
| 6,689,205 B1 | 2/2004 | Bruckner et al. |
| 6,689,934 B2 | 2/2004 | Dodge et al. |
| 6,700,035 B2 | 3/2004 | Yoshimasa |
| 6,702,800 B1 | 3/2004 | Vukos et al. |
| 6,730,069 B2 | 5/2004 | Tanzer et al. |
| 6,790,798 B1 | 9/2004 | Suzuki et al. |
| 6,797,360 B2 | 9/2004 | Varona |
| 6,849,672 B2 | 2/2005 | Mehawej et al. |
| 6,875,264 B2 | 4/2005 | Zimmermann et al. |
| 6,878,433 B2 | 4/2005 | Curro et al. |
| 6,899,776 B2 | 5/2005 | Bahlmann et al. |
| 6,965,058 B1 | 11/2005 | Raidel et al. |
| 6,972,011 B2 | 12/2005 | Maeda et al. |
| 7,321,007 B2 | 1/2008 | Gagliardi et al. |
| 7,699,825 B2 | 4/2010 | Nakagawa et al. |
| 7,722,590 B2 | 5/2010 | Tsuji et al. |
| 7,744,576 B2 | 6/2010 | Busam et al. |
| 7,750,203 B2 | 7/2010 | Becker et al. |
| 7,759,540 B2 | 7/2010 | Litvay et al. |
| 7,767,878 B2 | 8/2010 | Suzuki |
| 7,838,721 B2 | 11/2010 | Chen |
| 7,838,722 B2 | 11/2010 | Blessing et al. |
| 7,847,145 B2 | 12/2010 | Kurita et al. |
| 7,872,168 B2 | 1/2011 | Sawyer et al. |
| 7,994,233 B2 | 8/2011 | Mehawej et al. |
| 7,994,384 B2 | 8/2011 | Qin et al. |
| 8,148,598 B2 | 4/2012 | Tsang et al. |
| 8,163,124 B2 | 4/2012 | Moriura et al. |

(56) References Cited

U.S. PATENT DOCUMENTS

| | | | |
|---|---|---|---|
| 8,180,603 B2 | 5/2012 | Blessing et al. | |
| 8,187,240 B2 | 5/2012 | Busam et al. | |
| 8,211,076 B2 | 7/2012 | Sugiyama et al. | |
| 8,268,424 B1 | 9/2012 | Suzuki et al. | |
| 8,735,646 B2 | 5/2014 | Beruda et al. | |
| 8,802,918 B2 | 8/2014 | Fukudome et al. | |
| 8,901,367 B2 | 12/2014 | Sanz et al. | |
| 8,979,815 B2 | 3/2015 | Roe et al. | |
| 9,072,634 B2 | 7/2015 | Hundorf et al. | |
| 9,107,777 B2 | 8/2015 | Kinoshita et al. | |
| 9,216,118 B2 | 12/2015 | Roe et al. | |
| 9,233,519 B2 | 1/2016 | Yamaguchi et al. | |
| 9,237,974 B2 | 1/2016 | Ohashi et al. | |
| 9,295,593 B2 | 3/2016 | Van Malderen | |
| 9,468,566 B2 | 10/2016 | Rosati et al. | |
| 9,486,371 B2 | 11/2016 | Wirtz et al. | |
| 9,549,858 B2 | 1/2017 | Yang | |
| 9,707,135 B2 | 7/2017 | Sheldon et al. | |
| 9,713,557 B2 | 7/2017 | Arizti et al. | |
| 9,789,014 B2 | 10/2017 | Wright et al. | |
| 10,071,002 B2 | 9/2018 | Bianchi et al. | |
| 10,123,916 B2 | 11/2018 | Weisman et al. | |
| 10,307,298 B2 | 6/2019 | Varona et al. | |
| 10,675,195 B2 | 6/2020 | Greco et al. | |
| 10,772,769 B2 | 9/2020 | Maele | |
| 2002/0115969 A1 | 8/2002 | Maeda et al. | |
| 2003/0097105 A1 | 5/2003 | Chen et al. | |
| 2003/0119394 A1 | 6/2003 | Ranganathan et al. | |
| 2003/0119402 A1 | 6/2003 | Melius et al. | |
| 2003/0120231 A1 | 6/2003 | Wang et al. | |
| 2003/0129915 A1 | 7/2003 | Harriz | |
| 2003/0139719 A1 | 7/2003 | Nanaumi et al. | |
| 2003/0143376 A1 | 7/2003 | Toyoshima et al. | |
| 2003/0149414 A1 | 8/2003 | Mehawej | |
| 2003/0167046 A1 | 9/2003 | Klemp et al. | |
| 2003/0175418 A1 | 9/2003 | Muthiah et al. | |
| 2004/0015142 A1 | 1/2004 | Johnston et al. | |
| 2004/0054342 A1 | 3/2004 | Newbill et al. | |
| 2004/0111848 A1 | 6/2004 | Miyamoto et al. | |
| 2004/0116014 A1 | 6/2004 | Soerens et al. | |
| 2004/0167486 A1 | 8/2004 | Busam et al. | |
| 2004/0204697 A1 | 10/2004 | Litvay | |
| 2004/0211361 A1 | 10/2004 | Suzuki et al. | |
| 2005/0165371 A1 | 7/2005 | Giacometti | |
| 2005/0166799 A1 | 8/2005 | Fuller et al. | |
| 2005/0171499 A1 | 8/2005 | Nigam et al. | |
| 2005/0215962 A1 | 9/2005 | Litvay et al. | |
| 2006/0004334 A1 | 1/2006 | Schlinz et al. | |
| 2006/0021695 A1 | 2/2006 | Blessing et al. | |
| 2006/0167424 A1 | 7/2006 | Chang et al. | |
| 2007/0093164 A1 | 4/2007 | Nakaoka | |
| 2007/0197987 A1* | 8/2007 | Tsang | A61F 13/536 604/365 |
| 2008/0103466 A1 | 5/2008 | Ehmsperger et al. | |
| 2008/0215166 A1 | 9/2008 | Blessing et al. | |
| 2009/0005752 A1 | 1/2009 | Suzuki et al. | |
| 2009/0076473 A1 | 3/2009 | Kasai et al. | |
| 2009/0087636 A1* | 4/2009 | Yasuda | A61L 15/60 428/220 |
| 2009/0112175 A1 | 4/2009 | Bissah et al. | |
| 2010/0057032 A1 | 3/2010 | Hardegree | |
| 2010/0063470 A1 | 3/2010 | Suzuki et al. | |
| 2010/0100065 A1 | 4/2010 | Bianco et al. | |
| 2011/0046597 A1 | 2/2011 | Mizutani et al. | |
| 2011/0111199 A1 | 5/2011 | Takatori et al. | |
| 2011/0151228 A1 | 6/2011 | Takatori et al. | |
| 2011/0276019 A1 | 11/2011 | Kakimoto et al. | |
| 2012/0029456 A1 | 2/2012 | Takatori et al. | |
| 2012/0071852 A1 | 3/2012 | Tsang et al. | |
| 2012/0089108 A1 | 4/2012 | Ueda et al. | |
| 2012/0175056 A1 | 7/2012 | Tsang et al. | |
| 2012/0203191 A1 | 8/2012 | Maruo et al. | |
| 2012/0238977 A1 | 9/2012 | Oku et al. | |
| 2012/0288701 A1 | 11/2012 | Matsushita et al. | |
| 2012/0308799 A1 | 12/2012 | Yamaguchi et al. | |
| 2012/0328861 A1 | 12/2012 | Hinayama et al. | |
| 2012/0328862 A1 | 12/2012 | Fukudome et al. | |
| 2013/0018349 A1 | 1/2013 | Takatori et al. | |
| 2013/0046263 A1 | 2/2013 | Fukudome et al. | |
| 2013/0072890 A1 | 3/2013 | Yang | |
| 2013/0116644 A1 | 5/2013 | Wei et al. | |
| 2013/0178814 A1 | 7/2013 | Matsushita et al. | |
| 2013/0284361 A1 | 10/2013 | Tsujimoto et al. | |
| 2014/0180230 A1 | 6/2014 | Tsang et al. | |
| 2014/0276508 A1 | 9/2014 | Wright et al. | |
| 2014/0276518 A1 | 9/2014 | Varona et al. | |
| 2014/0296817 A1 | 10/2014 | Malderen | |
| 2014/0303582 A1 | 10/2014 | Wright et al. | |
| 2015/0005727 A1 | 1/2015 | Matsushita et al. | |
| 2015/0038929 A1 | 2/2015 | Malderen | |
| 2016/0151213 A1 | 6/2016 | Bauduin et al. | |

FOREIGN PATENT DOCUMENTS

| | | |
|---|---|---|
| EP | 0212618 A1 | 3/1987 |
| EP | 0719531 A1 | 7/1996 |
| EP | 0829245 A2 | 3/1998 |
| EP | 0725616 B1 | 3/1999 |
| EP | 0947549 A1 | 10/1999 |
| EP | 1428581 A1 | 6/2004 |
| EP | 1447066 A1 | 8/2004 |
| EP | 1447067 A1 | 8/2004 |
| EP | 1561442 A1 | 8/2005 |
| EP | 1609448 A1 | 12/2005 |
| EP | 1621166 A1 | 2/2006 |
| EP | 1627618 A1 | 2/2006 |
| EP | 1800638 A1 | 6/2007 |
| EP | 2550946 A1 | 1/2013 |
| EP | 2986263 B1 | 1/2017 |
| EP | 2086487 B1 | 9/2018 |
| GB | 2252047 A | 7/1992 |
| JP | H06190001 A | 7/1994 |
| JP | H10137291 A | 5/1998 |
| JP | 2002159533 A | 6/2002 |
| JP | 2002345883 A | 12/2002 |
| JP | 2003284743 A | 10/2003 |
| JP | 2007236911 A | 9/2007 |
| JP | 2010051697 A | 3/2010 |
| JP | 2010136880 A | 6/2010 |
| JP | 4795612 B2 | 10/2011 |
| JP | 2012075638 A | 4/2012 |
| JP | 2012125597 A | 7/2012 |
| JP | 2012192165 A | 10/2012 |
| JP | 2013010361 A | 1/2013 |
| KR | 100376944 B1 | 6/2003 |
| KR | 100494196 B1 | 9/2005 |
| WO | 1995003019 A1 | 2/1995 |
| WO | 1995021596 A1 | 8/1995 |
| WO | 2000041663 A1 | 7/2000 |
| WO | 2004098473 A1 | 11/2004 |
| WO | 2006007185 A1 | 1/2006 |
| WO | 2007098492 A2 | 8/2007 |
| WO | 2010143635 A1 | 12/2010 |
| WO | 2011128790 A2 | 10/2011 |
| WO | 2012048878 A1 | 4/2012 |
| WO | 2012108331 A1 | 8/2012 |
| WO | 2013099634 A1 | 7/2013 |
| WO | 2015002934 A2 | 1/2015 |

OTHER PUBLICATIONS

Supplementary EP Search Report issued in EP Application No. 14763071.9 dated Jan. 23, 2017 [18 pages].

2nd Office Action from Chinese Application No. 200780014162.9 filed Feb. 22, 2007, dated Aug. 29, 2012, 7pages.

3rd Office Action from Chinese Application No. 200780014162.9 filed Feb. 22, 2007, dated Feb. 27, 2013, 8 pages.

International Preliminary Report on Patentability dated Aug. 26, 2008, during the prosecution of International Application No. PCT/US2007/062614.

International Search Report dated Aug. 27, 2014, during the prosecution of International Application No. PCT/JS2014/030066.

(56) References Cited

OTHER PUBLICATIONS

International Search Report dated Dec. 17, 2007, and published Feb. 21, 2008, during the prosecution of International Application No. PCT/US2007/062614.
International Search Report dated Jan. 12, 2015, during the prosecution of International Application No. PCT/US2014/045027.
International Search Report dated Jul. 30, 2014, during the prosecution of International Application No. PCT/US2014/026148.
International Search Report dated Oct. 28, 2014, during the prosecution of International Application No. PCT/US2014/030051.
Notification of Transmittal of International Preliminary Report on Patentability dated Nov. 24, 2015, during the prosecution of International Application No. PCT/US2014/030051; 48 pages.
Office Action from Chinese Application No. 200780014162.9 filed Feb. 22, 2007, dated Feb. 29, 2012, 9 pages.
Partial Supplementary EP Search Report, issued in EP Application No. 14763071.9 dated Sep. 23, 2016 [9 pages].
Written Opinion dated Aug. 27, 2014, during the prosecution of International Application No. PCT/US2014/030066.
Written Opinion dated Dec. 17, 2007, and published Aug. 22, 2008 during the prosecution of International Application No. PCT/US2007/062614.
Written Opinion dated Jan. 12, 2015, during the prosecution of International Application No. PCT/US2014/045027.
Written Opinion dated Jul. 30, 2014, during the prosecution of International Application No. PCT/US2014/026148.
Written Opinion dated Oct. 28, 2014, during the prosecution of International Application No. PCT/US2014/030051.
Written Opinion of the International Preliminary Examining Authority dated Jun. 5, 2015, during the prosecution of International Application No. PCT/US2014/030051; 32 pages.
First Examination Report issued in corresponding New Zealand Patent Application No. 713158, dated Jul. 19, 2017; [8 pages].

* cited by examiner

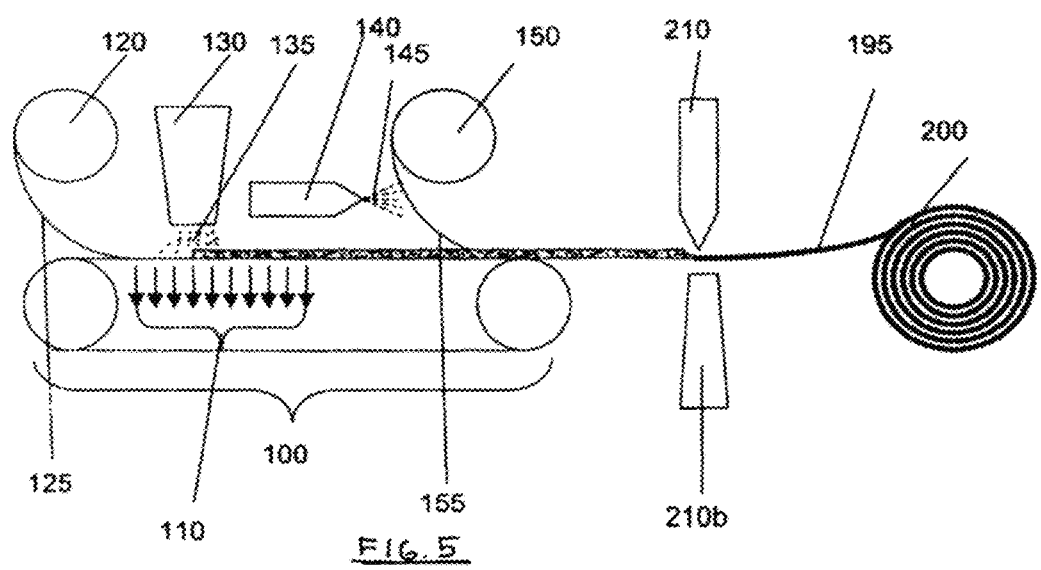

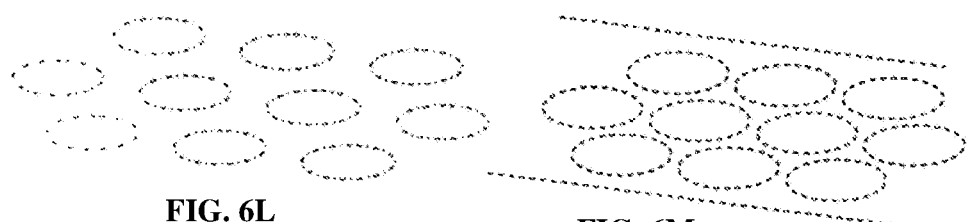
FIG. 6L  FIG. 6M
FIG. 6N
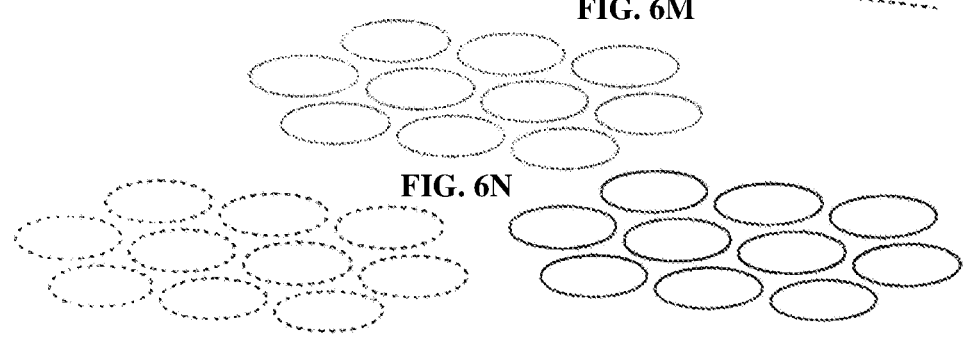
FIG. 6O  FIG. 6P
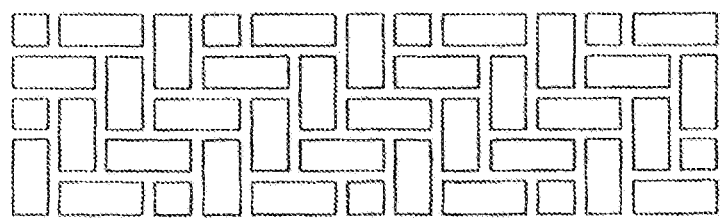
FIG. 6Q

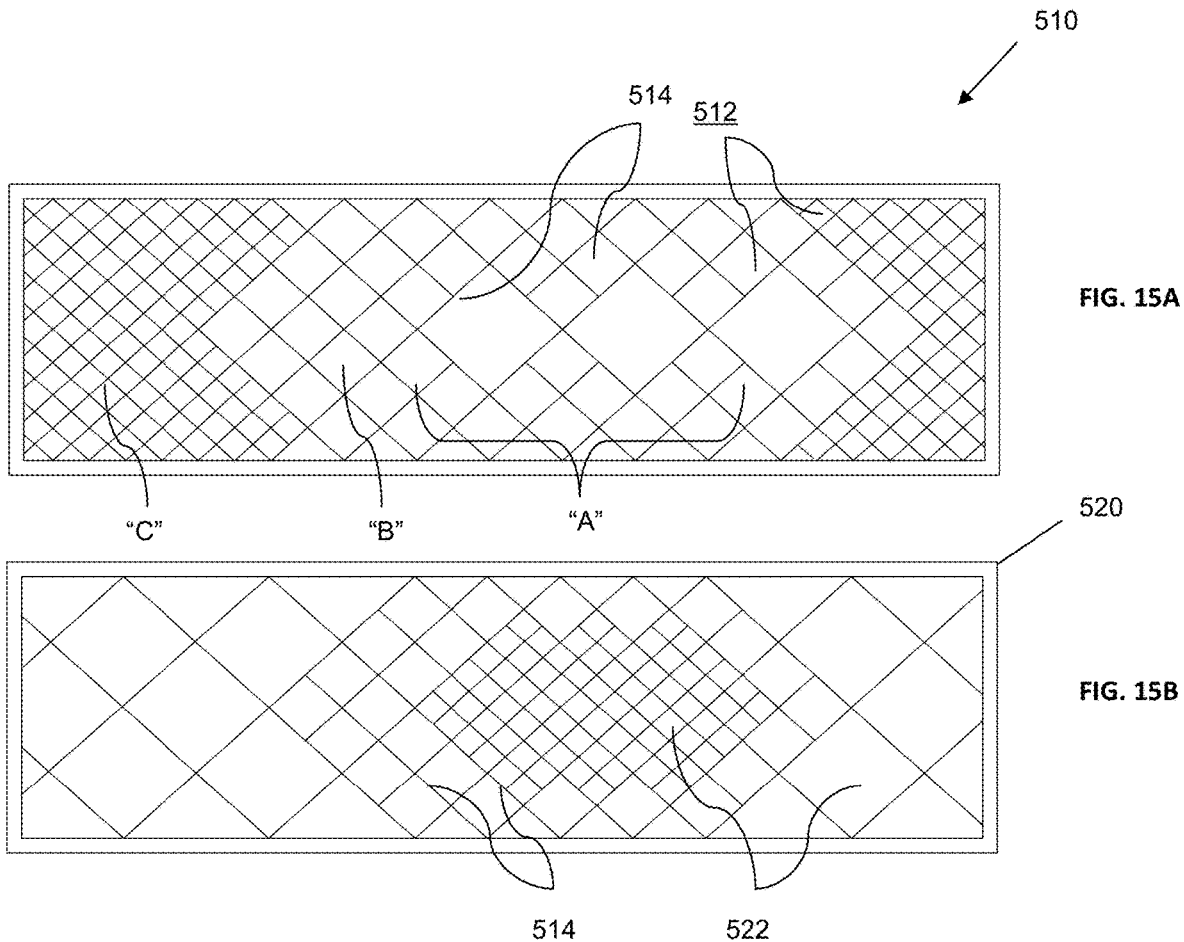

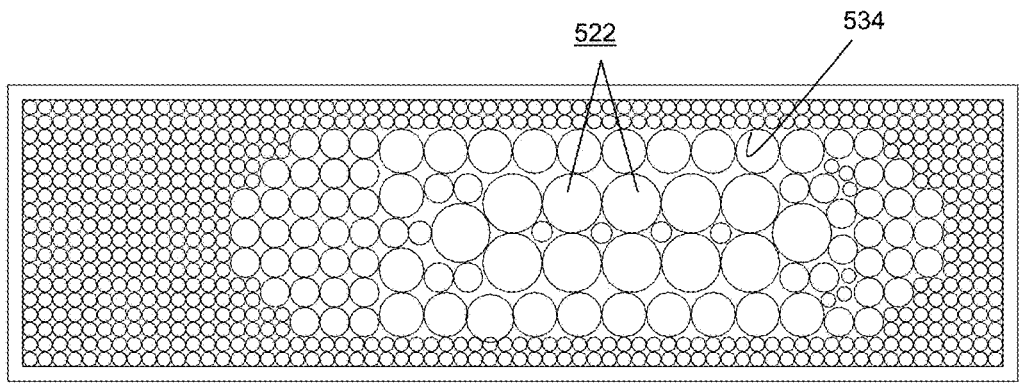
FIG. 15C
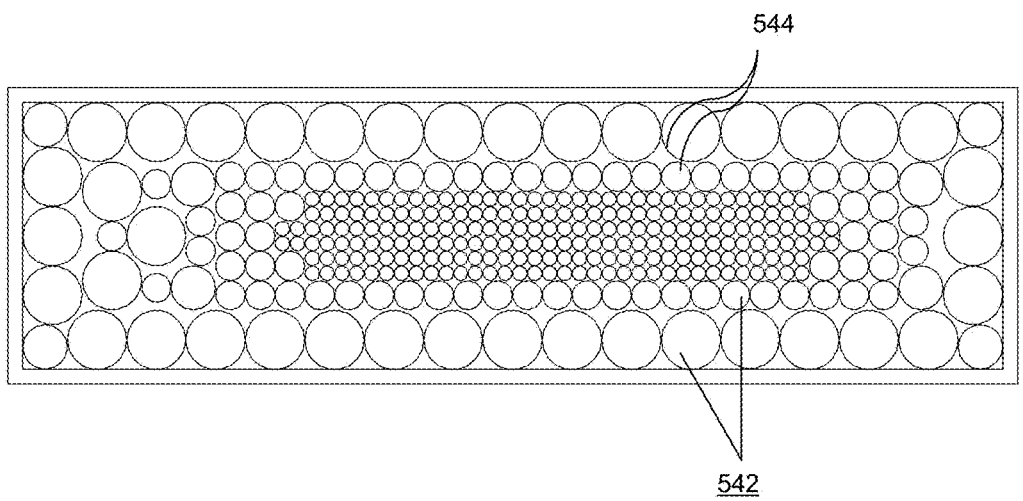
FIG. 15D
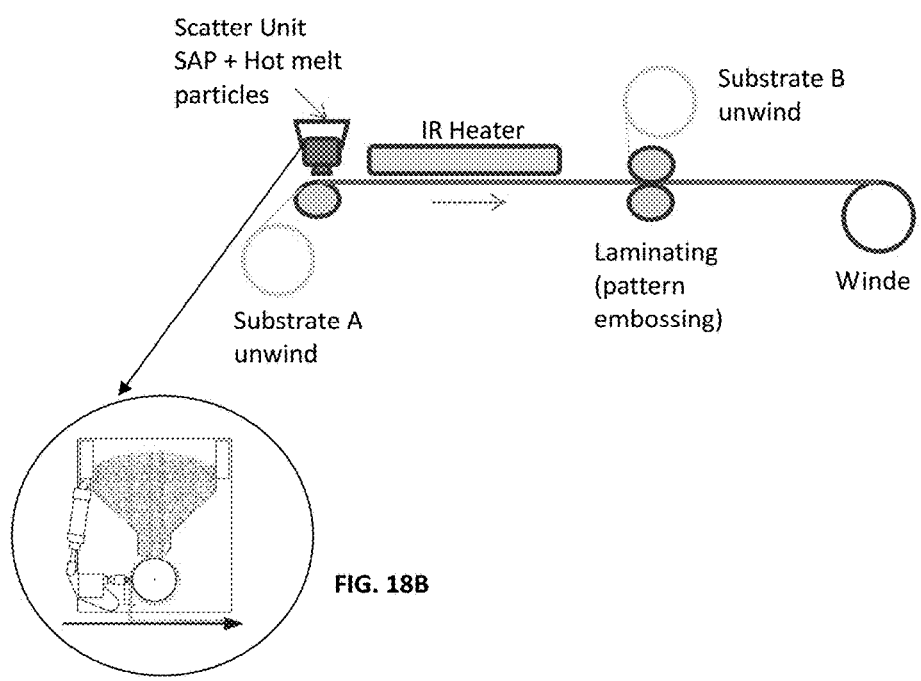
FIG. 18A
FIG. 18B

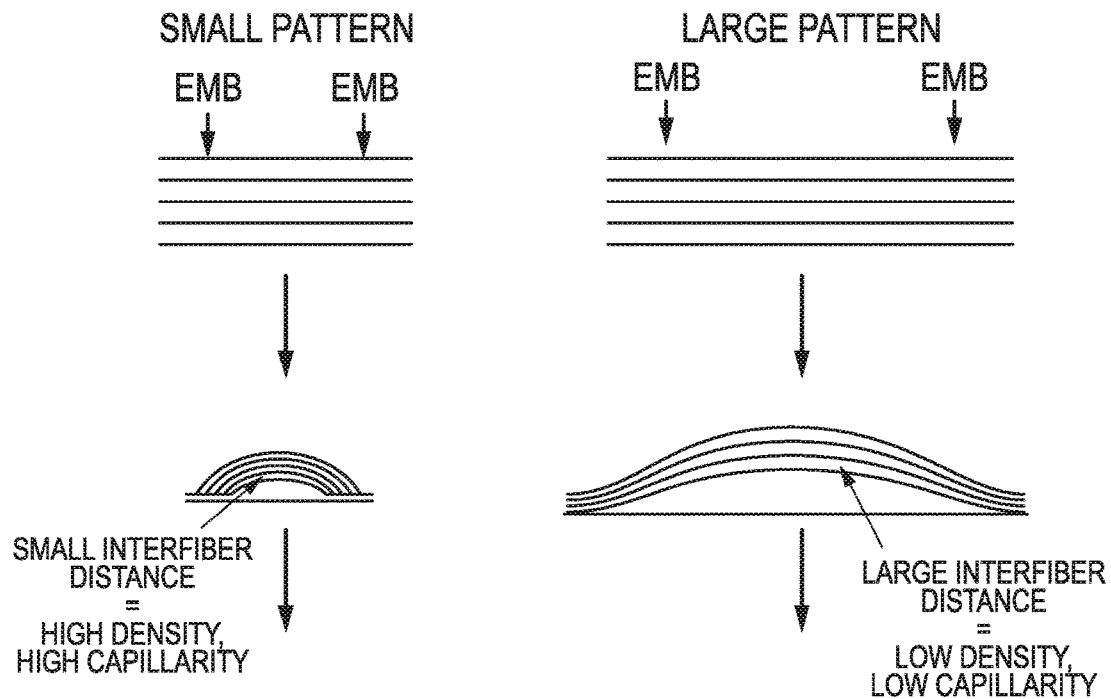
FIG. 17A
FIG. 17B
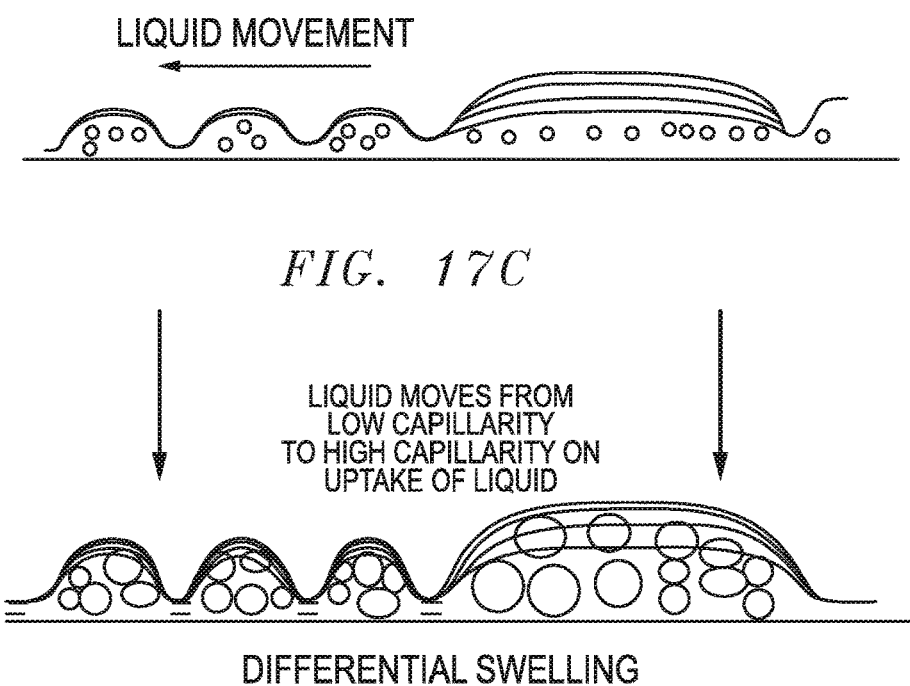
FIG. 17C
FIG. 17D

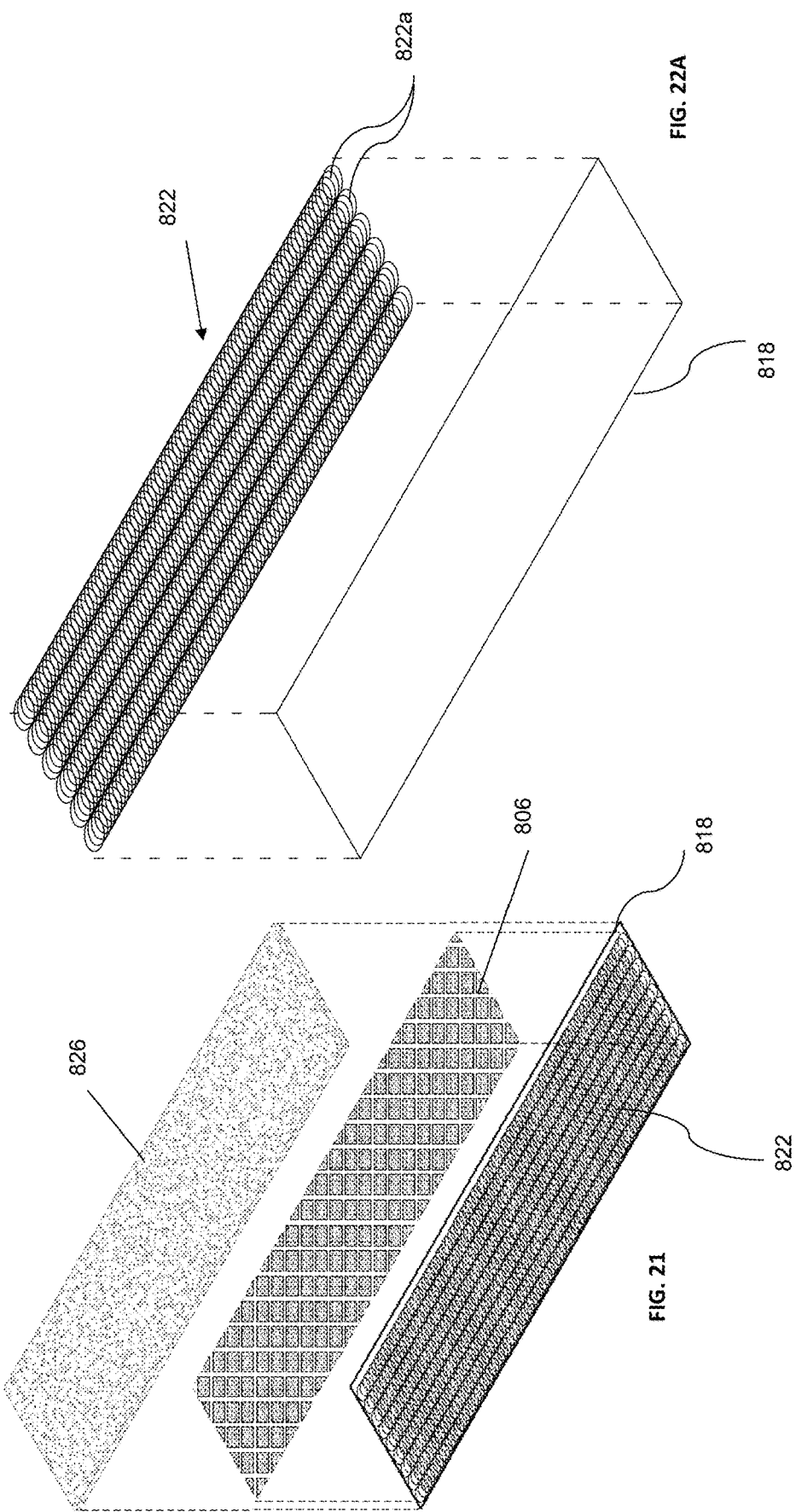

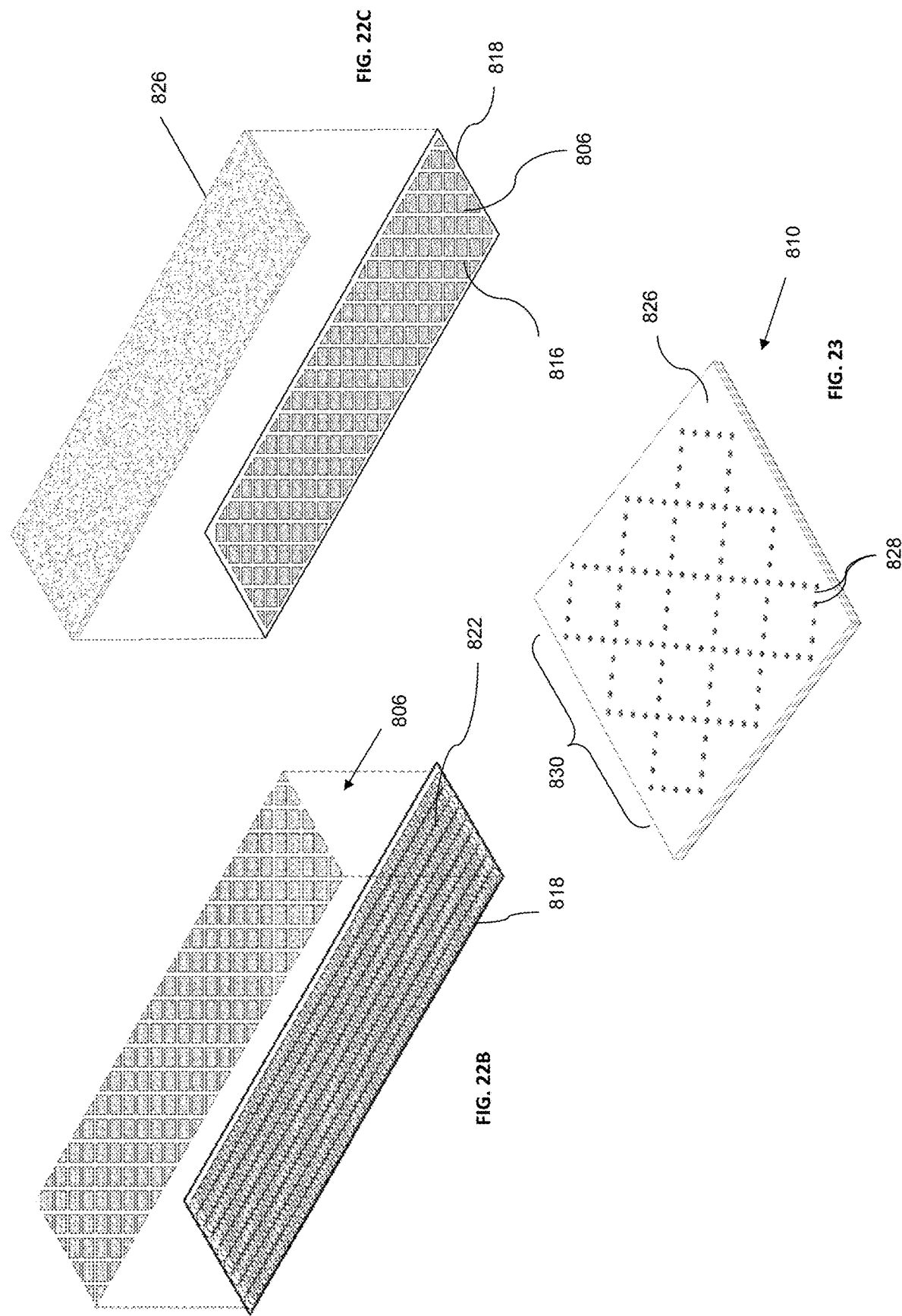

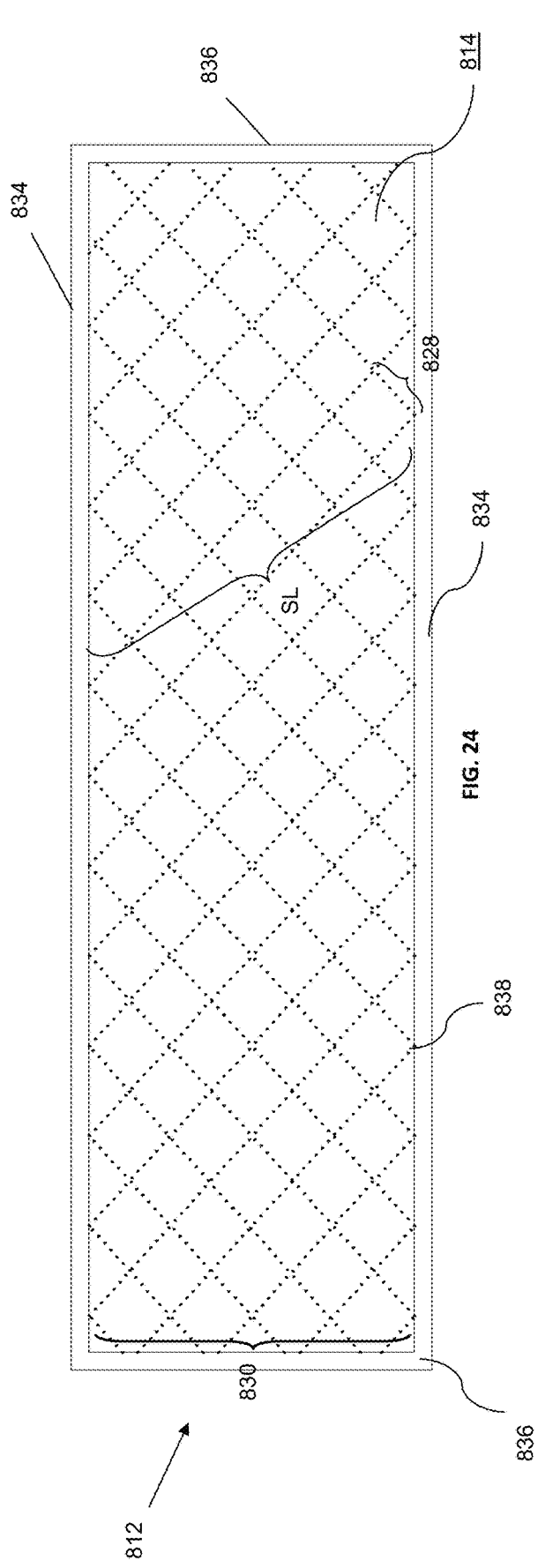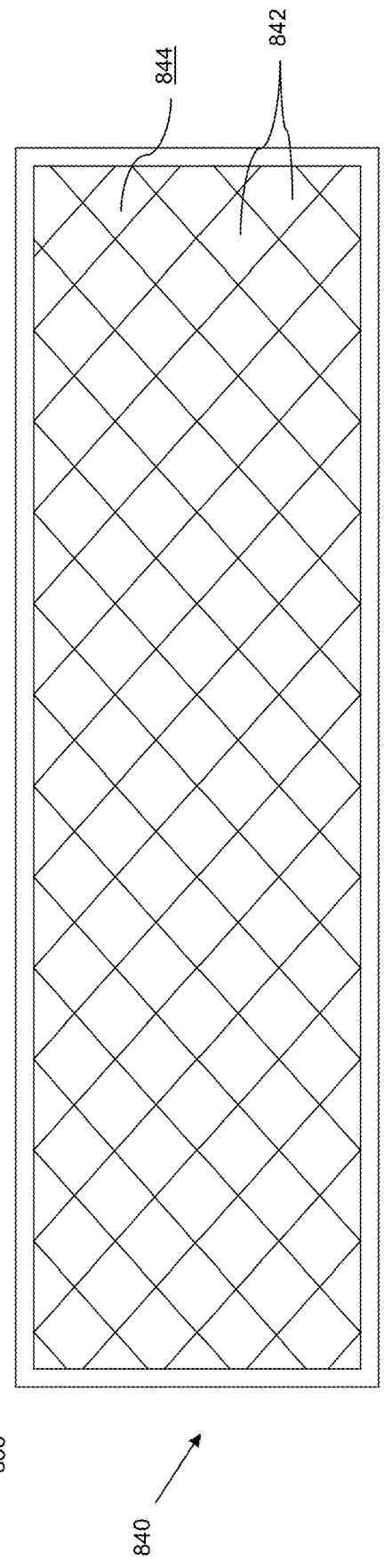

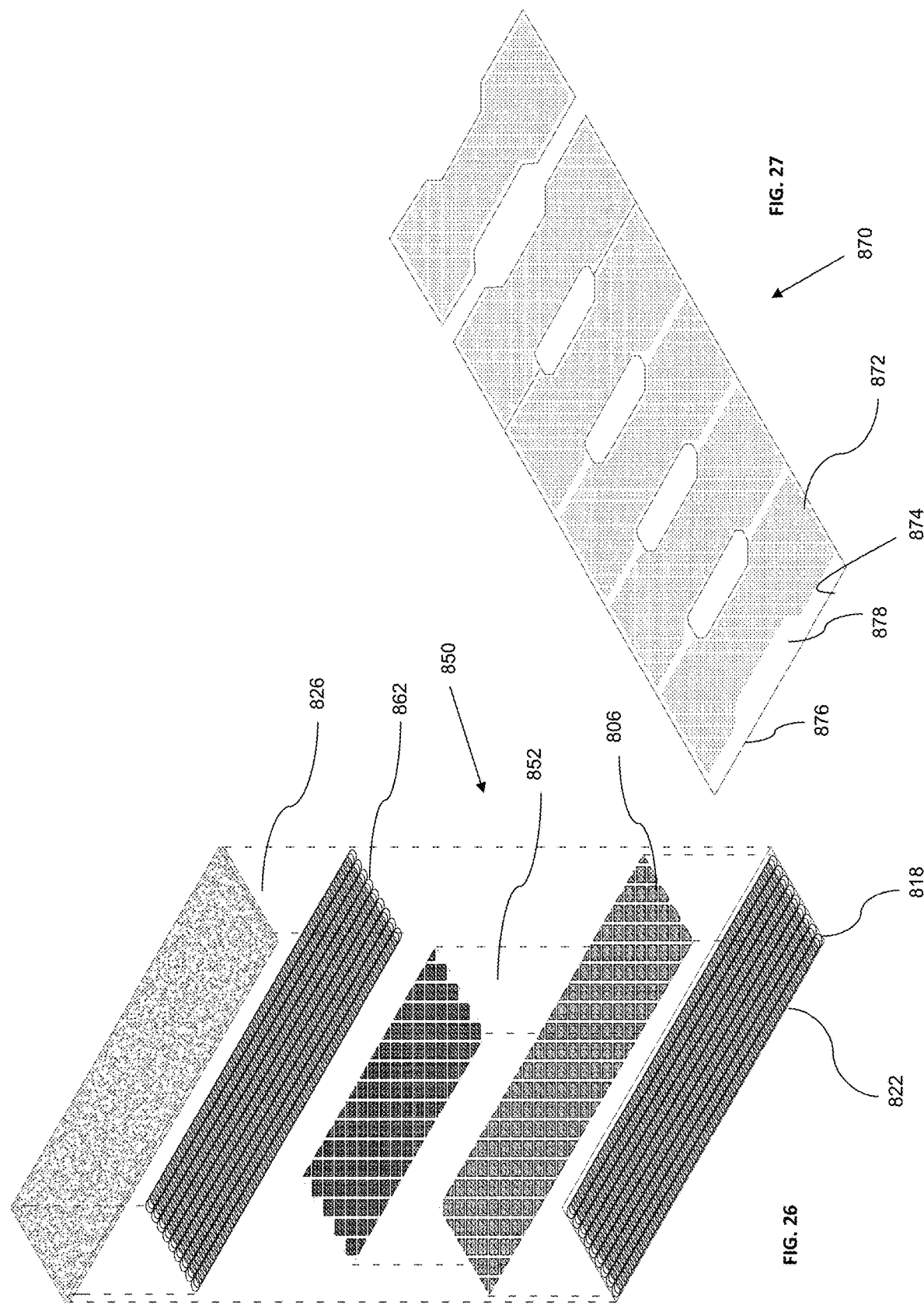

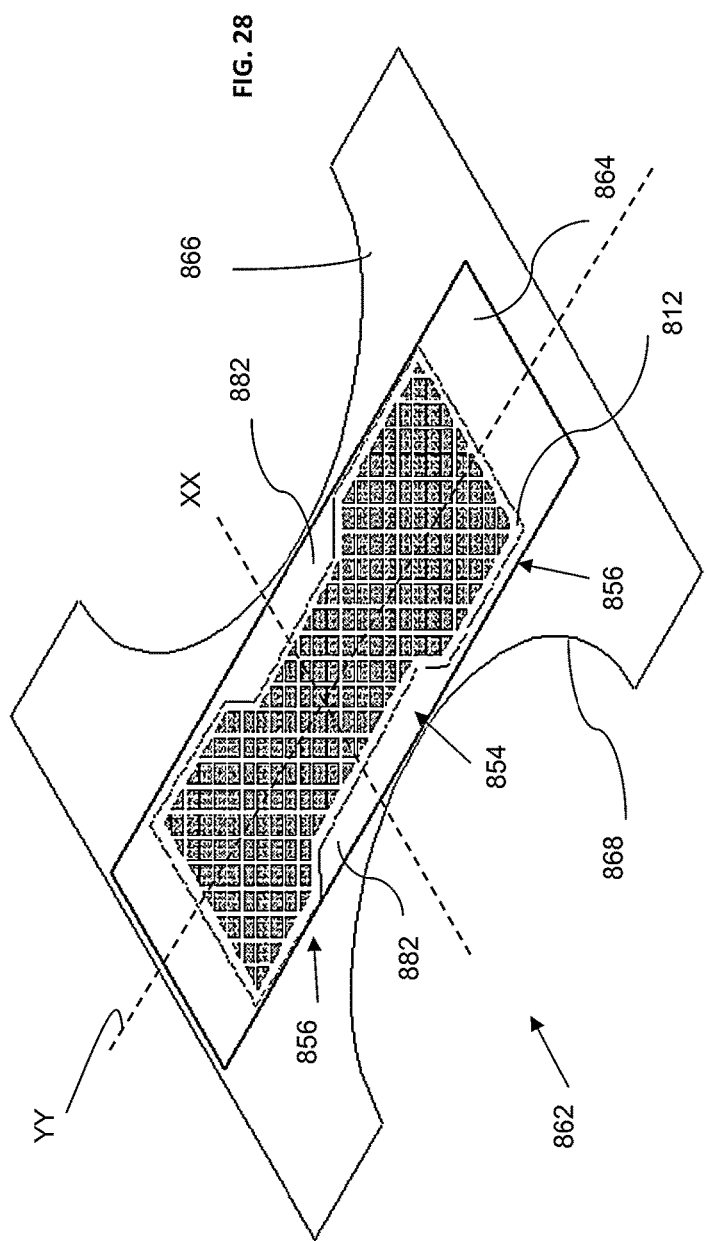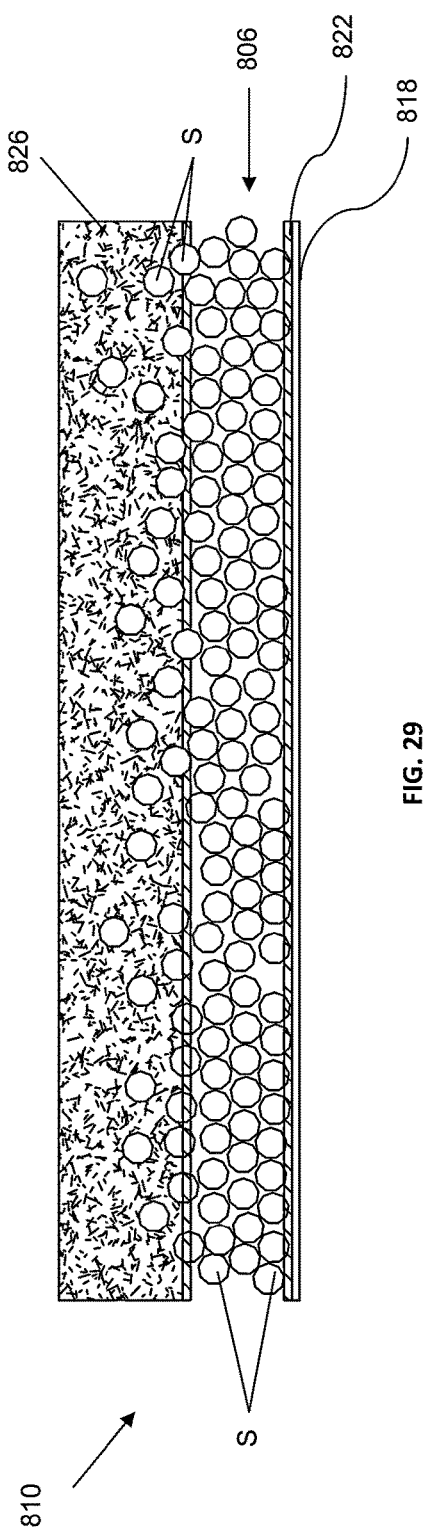

FIG. 31

Web Density

| | | 0.01 | 0.02 | 0.03 | 0.04 | 0.05 | 0.06 | 0.07 | 0.08 | 0.09 | 0.1 | 0.15 | 0.2 | 0.3 |
|---|---|---|---|---|---|---|---|---|---|---|---|---|---|---|
| Basis Weight | 15 | 1500 | 750 | 500 | 375 | 300 | 250 | 214 | 188 | 167 | 150 | 100 | 75 | 50 |
| | 20 | 2000 | 1000 | 667 | 500 | 400 | 333 | 286 | 250 | 222 | 200 | 133 | 100 | 67 |
| | 30 | 3000 | 1500 | 1000 | 750 | 600 | 500 | 429 | 375 | 333 | 300 | 200 | 150 | 100 |
| | 40 | 4000 | 2000 | 1333 | 1000 | 800 | 667 | 571 | 500 | 444 | 400 | 267 | 200 | 133 |
| | 50 | 5000 | 2500 | 1667 | 1250 | 1000 | 833 | 714 | 625 | 556 | 500 | 333 | 250 | 167 |
| | 60 | 6000 | 3000 | 2000 | 1500 | 1200 | 1000 | 857 | 750 | 667 | 600 | 400 | 300 | 200 |
| | 70 | 7000 | 3500 | 2333 | 1750 | 1400 | 1167 | 1000 | 875 | 778 | 700 | 467 | 350 | 233 |
| | 80 | 8000 | 4000 | 2667 | 2000 | 1600 | 1333 | 1143 | 1000 | 889 | 800 | 533 | 400 | 267 |
| | 90 | 9000 | 4500 | 3000 | 2250 | 1800 | 1500 | 1286 | 1125 | 1000 | 900 | 600 | 450 | 300 |
| | 100 | 10000 | 5000 | 3333 | 2500 | 2000 | 1667 | 1429 | 1250 | 1111 | 1000 | 667 | 500 | 333 |
| | 110 | 11000 | 5500 | 3667 | 2750 | 2200 | 1833 | 1571 | 1375 | 1222 | 1100 | 733 | 550 | 367 |
| | 120 | 12000 | 6000 | 4000 | 3000 | 2400 | 2000 | 1714 | 1500 | 1333 | 1200 | 800 | 600 | 400 |
| | 130 | 13000 | 6500 | 4333 | 3250 | 2600 | 2167 | 1857 | 1625 | 1444 | 1300 | 867 | 650 | 433 |
| | 140 | 14000 | 7000 | 4667 | 3500 | 2800 | 2333 | 2000 | 1750 | 1556 | 1400 | 933 | 700 | 467 |
| | 150 | 15000 | 7500 | 5000 | 3750 | 3000 | 2500 | 2143 | 1875 | 1667 | 1500 | 1000 | 750 | 500 |
| | 160 | 16000 | 8000 | 5333 | 4000 | 3200 | 2667 | 2286 | 2000 | 1778 | 1600 | 1067 | 800 | 533 |
| | 170 | 17000 | 8500 | 5667 | 4250 | 3400 | 2833 | 2429 | 2125 | 1889 | 1700 | 1133 | 850 | 567 |
| | 180 | 18000 | 9000 | 6000 | 4500 | 3600 | 3000 | 2571 | 2250 | 2000 | 1800 | 1200 | 900 | 600 |
| | 190 | 19000 | 9500 | 6333 | 4750 | 3800 | 3167 | 2714 | 2375 | 2111 | 1900 | 1267 | 950 | 633 |
| | 200 | 20000 | 10000 | 6667 | 5000 | 4000 | 3333 | 2857 | 2500 | 2222 | 2000 | 1333 | 1000 | 667 |

FIG. 32

| Fiber Type | Fiber Denier | Fiber Density | Web Density 0.01 | 0.02 | 0.03 | 0.04 | 0.05 | 0.06 | 0.07 | 0.08 | 0.09 | 0.1 | 0.15 | 0.2 | 0.3 |
|---|---|---|---|---|---|---|---|---|---|---|---|---|---|---|---|
| Polyolefin (PP or PE) | 1.5 | 0.91 | 1374 | 680 | 448 | 332 | 263 | 216 | 183 | 158 | 139 | 124 | 77 | 54 | 31 |
|  | 3 | 0.91 | 1944 | 961 | 633 | 470 | 371 | 306 | 259 | 224 | 197 | 175 | 109 | 77 | 44 |
|  | 6 | 0.91 | 2749 | 1359 | 896 | 664 | 525 | 433 | 366 | 317 | 278 | 247 | 155 | 108 | 62 |
|  | 12 | 0.91 | 3887 | 1922 | 1267 | 939 | 743 | 612 | 518 | 448 | 394 | 350 | 219 | 153 | 88 |
|  | 20 | 0.91 | 5018 | 2481 | 1636 | 1213 | 959 | 790 | 669 | 579 | 508 | 452 | 283 | 198 | 113 |
| Polyester (PET, PLA) | 1.5 | 1.3 | 1648 | 818 | 541 | 402 | 319 | 264 | 224 | 195 | 172 | 153 | 98 | 70 | 43 |
|  | 3 | 1.3 | 2331 | 1156 | 765 | 569 | 452 | 373 | 317 | 276 | 243 | 217 | 139 | 99 | 60 |
|  | 6 | 1.3 | 3296 | 1635 | 1082 | 805 | 639 | 528 | 449 | 390 | 344 | 307 | 196 | 141 | 85 |
|  | 12 | 1.3 | 4662 | 2313 | 1530 | 1138 | 903 | 747 | 635 | 551 | 486 | 434 | 277 | 199 | 120 |
|  | 20 | 1.3 | 6018 | 2986 | 1975 | 1470 | 1166 | 964 | 820 | 711 | 627 | 560 | 358 | 257 | 156 |
| PET/PE Bicomponent | 1.5 | 1.1 | 1514 | 750 | 495 | 368 | 292 | 241 | 204 | 177 | 156 | 139 | 88 | 63 | 37 |
|  | 3 | 1.1 | 2141 | 1061 | 701 | 521 | 412 | 340 | 289 | 250 | 220 | 196 | 124 | 88 | 52 |
|  | 6 | 1.1 | 3028 | 1500 | 991 | 736 | 583 | 481 | 409 | 354 | 312 | 278 | 176 | 125 | 74 |
|  | 12 | 1.1 | 4282 | 2121 | 1401 | 1041 | 825 | 681 | 578 | 501 | 441 | 393 | 249 | 177 | 105 |
|  | 20 | 1.1 | 5528 | 2739 | 1809 | 1344 | 1065 | 879 | 746 | 647 | 569 | 507 | 321 | 228 | 135 |
| Cellulosic (Rayon) | 1.5 | 1.5 | 1772 | 880 | 583 | 434 | 345 | 285 | 243 | 211 | 186 | 167 | 107 | 77 | 48 |
|  | 3 | 1.5 | 2506 | 1245 | 824 | 614 | 488 | 404 | 344 | 299 | 264 | 235 | 151 | 109 | 67 |
|  | 6 | 1.5 | 3544 | 1760 | 1166 | 868 | 690 | 571 | 486 | 422 | 373 | 333 | 214 | 155 | 95 |
|  | 12 | 1.5 | 5013 | 2489 | 1648 | 1228 | 976 | 807 | 687 | 597 | 527 | 471 | 303 | 219 | 135 |
|  | 20 | 1.5 | 6471 | 3214 | 2128 | 1585 | 1260 | 1042 | 887 | 771 | 680 | 608 | 391 | 282 | 174 |

METHOD OF MAKING AN ABSORBENT COMPOSITE

The present application is a Continuation application of U.S. application Ser. No. 14/214,868, filed on Mar. 15, 2014 (now U.S. Pat. No. 9,789,014), which is a Continuation-in-Part of U.S. application Ser. No. 14/026,927 filed on Sep. 13, 2013 (now U.S. Pat. No. 9,566,198), which claims the benefit of U.S. Provisional Application Ser. No. 60/801,620, filed on Mar. 15, 2013, which disclosures are hereby incorporated by reference for all purposes and made a part of the present disclosure.

BACKGROUND

The present disclosure relates generally to an absorbent composite (or absorbent core laminate) and a method of making an absorbent composite. The present invention also relates generally to disposable absorbent articles employing absorbent composites and methods of making same. Such disposable absorbent articles include diapers, training pants, adult incontinence products, bodily exudates absorbing products, feminine hygiene products, and other absorbent products (collectively "disposable absorbent articles" or "disposable absorbent products").

Disposable absorbent articles typically employ three basic structural elements: a topsheet that forms the inner surface, a backsheet that forms the outer surface, and an absorbent core that is interposed between the topsheet and the backsheet. The topsheet is designed to allow liquid to pass from outside the absorbent article through the topsheet and into the absorbent core. The topsheet may be made out of a range of liquid and vapor permeable hydrophilic or hydrophobic materials. The permeability of the topsheet can be increased by using surface activation agents ("surfactants"). Surfactants lower the surface energy or the contact angle of the liquid-solid interface and facilitate the liquid's passage through the topsheet.

The backsheet is designed to prevent fluid from passing from the absorbent core through the backsheet and out of the absorbent article. The backsheet may be made out of an impermeable film that extends the full width of the article or a combination of cloth-like material and impermeable film. The backsheet may also have vapor transmission properties ("breathability") that allow vapor to pass through the backsheet without releasing fluid stored in the absorbent core. The backsheet may also be made from a liquid impermeable but vapor transmitable non-woven material such as spun-bond, melt-blow, spun-bond ("SMS"); spun-bond, melt-blown, melt-blown, spun-bond ("SMMS"); micro, nano, or splitable fibers; spun melt or spun laced; carded; and the like.

The absorbent core is designed to contain and distribute fluid that passes through the topsheet. A typical absorbent core is made out of a high or super absorbent polymer (SAP) stabilized by an absorbent matrix. SAP is commonly made out of materials such as polyvinyl alcohol, polyacrylates, various grafted starches, and cross-linked sodium polyacrylate. SAP can be in the form of particles, fibers, foams, web, spheres, agglomerates of regular or irregular shapes, and film. The absorbent matrix is typically a de-fiberized wood pulp or similar material. The absorbent matrix is very bulky relative to the topsheet, backsheet, and SAP. Most of a diaper's thickness comes from the absorbent core.

Increasingly, consumers of absorbent articles are demanding thinner absorbent articles. To meet these demands, manufactures are decreasing the thickness of absorbent articles by decreasing the amount of absorbent matrix used in absorbent cores. Although the resulting absorbent cores are thinner, they suffer in performance. As the amount of absorbent matrix is reduced, it is less effective in stabilizing the SAP—preventing the SAP from migrating within the absorbent core. As SAP migrates within the core, the absorbent core loses its effectiveness and no longer has uniform absorbency. For example, SAP that is not contained tends to bunch up in wetted areas and is inefficient for handling subsequent discharges.

Manufacturers have attempted to solve this problem by creating small, individual SAP pockets or by gluing the SAP. These solutions, however, have been largely unsuccessful. The SAP pockets merely limit the migration to movement within the pockets. However, because there is still a movement of the particles, the absorbent core does not exhibit uniform absorbency. Gluing the SAP stabilizes the SAP, but results in an uncomfortably stiff absorbent core and a loss in the SAP's swelling capacity. Applicants have also discovered that may of the methods to contain the SAP can negatively impact SAP and the absorbent core's capacity to receive and distribute intake.

Accordingly, there exists a need for an improved absorbent product that continues the trend of decreasing product thickness, while minimizing product stiffness and otherwise exhibiting excellent absorbency and fluid handling properties. The specification of U.S. Pat. No. 8,148,598, which is commonly assigned and designates at least one common inventor as the present application, describes a prior improvement to the state of the art and serves as background to the present disclosure. The '598 patent document is hereby incorporated by reference, in its entirety, for all purposes and made a part of the present disclosure. The present disclosure may, in one respect, be regarded as continuing and furthering the effort to provide improved absorbent products and methods of manufacturing.

BRIEF SUMMARY

In one aspect, the disclosure provides improved absorbent composites and methods of making the composite. Embodiments are disclosed that focus on the composition or arrangement of components of the absorbent composite. In one embodiment, an absorbent core composite for a disposable absorbent article has a first fabric, a body side second fabric, and a plurality of aggregates of superabsorbent particles (SAP) situated between the first fabric second fabric. About each of a plurality of the SAP aggregates, an arrangement of spaced apart bond sites secure the second fabric to the first fabric and form a pocket in which the SAP aggregate is secured between the first fabric and the second fabric. The body side second fabric is a bulky nonwoven including fibers that entangle at least some particles in the SAP aggregate. In preferred embodiments, a pattern of adhesive may be preapplied on the first fabric (e.g., a pattern having a plurality of intersecting loops defining open regions free of adhesive).

In another aspect, a method is disclosed for manufacturing an absorbent composite laminate for a disposable absorbent article. The method entails conveying a first fabric into position to receive superabsorbent particles (SAP) and depositing SAP on the first fabric to provide discrete aggregates of SAP. A second fabric of a bulky nonwoven is then conveyed and positioning relative the first fabric such that fibers of the bulky nonwoven entangle particles in a top layer of particles of the SAP aggregate. This secures, at least partly, the SAP aggregate therebetween. The first and second fabric are then bonded at a network of bond sites to form an elongated laminate having a plurality of pockets of SAP aggregate, whereby each pocket is defined by bond sites positioned about a SAP aggregate and securing the second fabric to the first fabric; and conveying the elongated laminate, whereby the bulky nonwoven and pockets inhibit SAP particle migration from said pockets. In preferred embodiments, the bond sites are bond points and/or the bond sites form diamond shaped pockets and a corresponding grid without any direct straight line paths to the side margins.

A disposable absorbent article is also disclosed having a chassis body defined by a first end margin and a second end margin longitudinally spaced from the first end margin, the end margins partially defining front and back waist regions that are fastenable about a waist of a user. The article further includes a topsheet, a backsheet, and an absorbent composite disposed between the topsheet and backsheet. The absorbent composite includes a first fabric, a second fabric bonded to said first fabric, absorbent particles secured between the first and second fabric. The first fabric is intermittently attached to the second fabric to define a plurality of pockets situated between the first fabric and the second fabric and containing an aggregate of superabsorbent particles (SAP), wherein discontinuous and spaced apart bond sites secure the first fabric with the second fabric. The second fabric is a bulky nonwoven material positioned on a bodyside of the absorbent composite and over the SAP aggregate such that fibers of the bulky nonwoven entangle superabsorbent particles, wherein the SAP aggregate is free of an absorbent matrix in a middle portion extending from beneath the bulky nonwoven material.

In another aspect, an absorbent composite is disclosed having a bulky nonwoven substrate, a top fabric bonded with the bulky nonwoven substrate, and a layer of superabsorbent particles (SAP) secured therebetween. Furthermore, hot melt adhesive is interspersed with the SAP to mutually secure the SAP with the bulky nonwoven substrate and top fabric. The top fabric may be tissue material in preferred embodiments.

In yet another aspect, a method is disclosed for manufacturing an absorbent composite. The method entails conveying a first substrate of a nonwoven material, delivering a mixture of superabsorbent particles (SAP) with hot melt adhesive particles onto the conveyed first substrate, and, as the first substrate with the mixture is conveyed, applying heat to the first substrate, thereby activating the hot melt adhesive particles and bonding the SAP with the hot melt particles and the first substrate. A second substrate is then applied atop the first substrate and SAP layer bonded therewith.

Other embodiments are disclosed in which aggregates of absorbent particles are strategically located and/or constituted between a top layer and a bottom layer, and across the expanse of the composite or core. By varying the position of the aggregates or the restrictions on the aggregates, the performance and capabilities of the absorbent composite may be managed or influenced. In certain embodiments, the aggregates of absorbent particles are situated in containers or pockets. In further embodiments, the size, spacing, arrangement, and\or geometry or shape of the containers or pockets are specifically provided to achieve certain core fluid handling properties.

In one embodiment, a disposable absorbent article includes a chassis body defined by a first end margin and a second end margin longitudinally spaced from the first end margin, the end margins partially defining front and back waist regions that are fastenable about a waist of a user. The article further includes a topsheet, a backsheet, and an absorbent composite disposed between the topsheet and backsheet. The topsheet and backsheet define longitudinal and lateral margins of the chassis body. The absorbent composite includes a first fabric and a second fabric bonded to the first fabric. Furthermore, absorbent particles are secured or adhered between the first and second fabric, wherein the first fabric is intermittently attached to the second fabric to define a plurality of containers situated between the first fabric and the second fabric and containing an aggregate of absorbent particles. The absorbent composite may include regions of containers of absorbent particles aggregates including a primary region having containers of a first size and a secondary region having a plurality of containers of a second size different from the first size.

The present disclosure is of an absorbent composite that, in some embodiments, does not require a SAP layer or SAP constituency with an absorbent matrix (i.e., free of an absorbent matrix, pulpless) and a novel method of making the absorbent composite. The present document also discloses an absorbent article that incorporates the absorbent composite. The absorbent composite provides for an absorbent article that can be made very thin and pliable, while at the same time retaining enough SAP to provide sufficient absorbency and dry and wet integrity (uniform absorbency). Although using the absorbent composite in a diaper is described, one skilled in the art would readily understand that an absorbent composite made according to the inventive process may be used in a wide variety of absorbent products.

The present disclosure is also directed to an improved absorbent article incorporating the absorbent composite. Further, the present disclosure is directed to methods of manufacturing the absorbent composite or the absorbent article in which the absorbent composite is employed.

In one example, a method is described for manufacturing a composite sheet, comprising the steps of positioning a first fabric to receive particles, depositing particles on the first fabric, applying adhesive to a second fabric, positioning the second fabric relative to the first fabric, and forming bond sites that extend between the first and second fabric. The method may further include an article in which the particles comprise SAP particles, skin care particles, odor absorbing particles, binder particles, ion exchange particles, and combinations thereof. Still further, the method may include the step of coating the particles with a hydrophobic material.

The method may include conforming the first fabric to a surface. The surface may include recesses that form pockets or containers in the first fabric when it is conformed to the surface. The SAP particles may be guided into the pockets formed in the first fabric. Suction may be used to conform the first fabric to the surface. The adhesive applied to the second fabric may be applied in a concentration sufficient to secure an effective amount of dry particles. That concentration is generally between 1 to 100 grams per square meter. More specifically, the adhesive may be applied in a concentration of between 5 and 75 grams per square meter, or even more optimally, between 12 and 50 grams per square meter. The adhesive may be applied in a manner such that the total amount of adhesive engaging particles is between 1 and 100 grams per square meter. The inventive method may further includes a step of applying adhesive to the first fabric before particles are deposited on the first fabric.

The bond sites suitable for the method may be bond lines, which may be continuous or discontinuous and may define pockets or other shapes and designs. Alternatively, the bond sites may be bond points. The bond sites may be spaced apart and positioned relative to particles and/or arranged to prevent straight line particle migration of more than 2 inches, and to present a gap between successive or pairs of bond points in an arrangement of bond points encircling a SAP aggregate, which communicates the pockets containing the SAP aggregate with adjacent pockets and/or the rest of the absorbent core.

Alternatively, the method entails positioning a first fabric to receive particles, positioning particles on the first fabric, securing the particles relative to the first fabric, positioning a second fabric over the particles, and forming bond sites that join the first fabric to the second fabric. The bond sites may be discrete points spaced to inhibit the migration of particles. The bond sites may also be bond lines spaced to inhibit the migration of particles, or bond lines that are connected to form a single bond line. The bond lines may be arranged to form pockets within which some particles are positioned. The particles may be SAP particles, skin care particles, odor absorbing particles, binder particles, ion exchange particles, and combinations thereof. The particles may be secured to the first fabric with adhesive, thermal plastic, or combinations thereof. In addition to or in the alternative, the particles may be secured to the second fabric with adhesive, thermal plastic, or combinations thereof. Furthermore, shapes may be formed in the first fabric for receiving particles.

A disposable absorbent article according to the disclosure may comprise a topsheet, a backsheet, and an absorbent core disposed therebetween. The absorbent core is an absorbent composite comprising a first fabric, a second fabric bonded to the first fabric, and particles secured between the first and second fabric. The particles may be SAP particles, skin care particles, odor absorbing particles, binder particles, ion exchange particles, combinations thereof, or in preferred embodiments consist of SAP.

Alternatively, an absorbent layer may be provided that is supported on the backsheet, such that a section of the backsheet provides the second fabric of the absorbent composite. The backsheet may further comprises a first backsheet layer, a second backsheet layer and SAP particles in a concentration of about 20 to 650 gsm (preferably greater than 50 gsm in some further embodiments) positioned there between and the second back sheet layer is an SMS having a basis weight in the range of about 10 gsm to 60 gsm. The absorbent layer may be adhered between the first and second fabric with an adhesive concentration of between 1 and 100 grams per square meter. The first fabric may be bonded to the second fabric at discrete points, which discrete points may define pockets. Further, the first fabric may be bonded to the second fabric along a plurality of bond lines, which bond lines may define pockets.

The absorbent core may also comprise a first fabric, a second fabric, bond sites at which the first fabric is connected to the second fabric; and an absorbent layer of particles adhered between the first and second fabric. The particles may be SAP particles and/or other beneficial particles. The absorbent layer may be supported underneath a section of the topsheet, such that the section of topsheet provides the second fabric of the absorbent composite. The absorbent layer may be supported on a section of the backsheet, such that the backsheet section provides the first fabric of the absorbent composite.

In some embodiments, the disposable absorbent article may include a concentration of SAP particles in the absorbent layer of between about 50 and 650 grams per square meter. The SAP particles may also be coated with a hydrophobic material to retard the initial receipt of liquid by the SAP particles in the absorbent layer. The bond sites may define a plurality of continuous lines that inhibit the movement of the SAP particles of the absorbent layer. The continuous lines may be shaped to form pockets between the first and second fabrics. The bond sites may define a plurality of discontinuous lines that inhibit the movement of the SAP particles of the absorbent layer. The discontinuous lines may be shaped to form pockets between the first and second fabric.

In the yet another embodiment, the bonds may be positioned along periphery of pockets of particles. The bonds may form a pattern such as herringbone, bricklayer, circles, triangles, dots, dashes, rectangles, and combinations thereof. The yet another embodiment may also include loose particles positioned between the first and second sheets.

The foregoing has outlined rather broadly the features and technical advantages of the present disclosure in order that the detailed description that follows may be better understood. Additional features and advantages will be described hereinafter. It should be appreciated that the specific embodiments disclosed may be readily utilized as a basis for modifying or designing other structures for carrying out the same purposes. It should also be realized that such equivalent constructions do not depart from the disclosure as set forth in the appended claims. The features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

This patent or patent application contains at least one drawing executed in color. Copies of this patent or patent application publication with color drawing(s) will be provided by the Office upon request and payment of the necessary fee.

For a more complete understanding of the present disclosure, reference is now made to the following descriptions taken in conjunction with the accompanying drawing, in which:

FIG. 5 is a variation of the method shown in FIG. 2 that uses ultrasonic bonding techniques instead of calendar rolls;

FIGS. 15A-15D are simplified illustrations of an absorbent composite according to the present disclosure, with particular attentions to an arrangement of aggregates of absorbent particles across the composite;

FIGS. 17A-17D are simplified illustrations in cross-sectional view of pockets and fluid properties characterizing the arrangement of pockets, in accordance with the disclosure;

FIG. 18A is a simplified schematic of a process of making an absorbent composite according to the disclosure;

FIGS. 18B-18C are illustrations or photographs of exemplary components of the process described in respect to FIG. 18A;

FIG. 21 is an exploded view of an absorbent core laminate according to an embodiment of the disclosure;

FIGS. 22A-22C are exploded view of various stages of manufacturing the laminate in FIG. 21;

FIG. 23 is a top perspective view of an embossed absorbent core laminate according to an embodiment of the disclosure;

FIG. 24 is a plan view of an exemplary absorbent core laminate employing bond points, according to an embodiment of the disclosure;

FIG. 25 is a plan view of an absorbent core laminate according to an alternate embodiment of the disclosure;

FIG. 26 is an exploded view of an absorbent core laminate according to an alternate embodiment of the disclosure;

FIG. 27 is simplified illustration of a stage in the manufacture of an absorbent core laminate according to an embodiment of the disclosure;

FIG. 28 is a plan view of a disposable absorbent article employing an absorbent core laminate, according to a preferred embodiment of the disclosure;

FIG. 29 is a simplified illustration in cross-sectional view of an absorbent composite according to a preferred embodiment of the disclosure.

FIG. 31 is a Table of web thickness (in microns) vs. basic weight and density; and FIG. 32 is a Table of pore diameter (in microns) vs. density at a given fiber size and fiber density.

DETAILED DESCRIPTION

Upon review of the detailed description and the accompanying drawings provided herein, it will be apparent to one of ordinary skill in the art that an absorbent composite made according to the present disclosure may be used in disposable absorbent articles, and more particularly, in disposable absorbent articles, such as diapers, training pants or other incontinence products. Accordingly, the present disclosure shall not be limited to the structures and processes specifically described and illustrated herein, although the following description is particularly directed to an absorbent composite that is used in a disposable diaper. The term "absorbent article" or "absorbent garment" with which the present disclosure is associated, includes various types of disposable articles and garments which are placed against or in proximity to the body of the wearer so as to absorb and contain various bodily exudates, bodily fluid, or biofluid.

Perhaps to gain a better understanding and appreciation of the particular contributions and improvements which are introduced in the present disclosure, reference may be first made to the improvements earlier disclosed in U.S. Pat. No. 8,148,598. These earlier improvements are described in respect to FIGS. 1-14. Some of the teachings and suggestions therein may, in addition to serving as background knowledge in the art, translate to certain specific embodiments of the present disclosure (which will become apparent to one skilled in the relevant art given the present disclosure).

Figure 1:
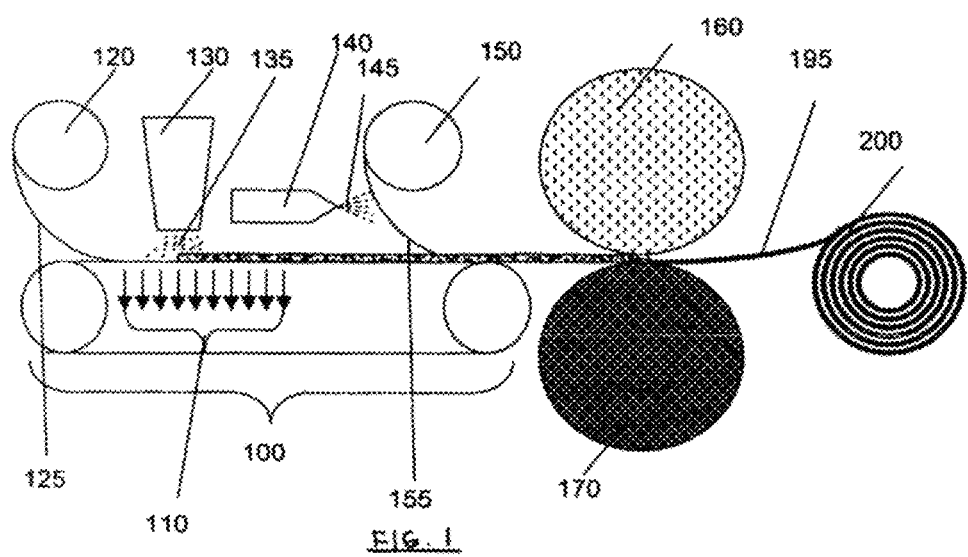
FIG. 1 is a schematic of one embodiment of a method of making an absorbent composite using calendar rolls.

In FIG. 1, a fabric 125 is shown as it is dispensed from roll 120 and carried along a production line on a conveyer belt 100 or other surface. The fabric 125 may be thermal plastic material that may be a woven, nonwoven, film, or a combination thereof. The fabric 125 is secured to the conveyer belt 100 (or other means) by a vacuum system 110. The vacuum system 110 serves to confirm the fabric 125 to the conveyer belt 100 (or other means).

In one embodiment, the surface of the conveyor belt 100 has recessed portions that form cups in the fabric 125 as the fabric is pulled against the surface of the conveyor belt 100. The surface of the conveyor belt 100 is not limited to constructions that form cups in the fabric but, instead, may be configured with a number of different surface shapes and sizes. Examples include ridges, raised shapes, and holes. In addition, the surface shapes may be distributed uniformly or non-uniformly across the width and length of the conveyor belt. Alternatively, the conveyor belt 100 may be flat. In applications in which the conveyor belt 100 has holes or other similar constructions, the depth of the pockets formed in the fabric 125 may be varied by the force of the vacuum system 110, the elasticity of the fabric 125, or a combination thereof. Additionally, heat may be used to increase the elasticity of the fabric 125 as the fabric is pulled against the surface of the conveyor belt 100. Heat may be applied to the fabric by way of a heated conveyor belt or any other means known in the art. The vacuum 110 may be applied uniformly across the surface of the conveyor belt 100 or at selected locations. For example, in a configuration in which the surface of conveyor belt 100 has depressions, vacuum may be applied only at the depressions.

The SAP particles 135 are then deposited on the fabric 125 by SAP dispenser 130. The SAP dispenser 130 may be configured to position SAP particles in their desired position on the first fabric or may be configured merely to deposit SAP particles on the first fabric, wherein the SAP particles are position by another means. One skilled the art understands that multiple SAP dispensers 130 may be used. The SAP particles 135 may be deposited, positioned, or both on the fabric 125 by wind or other known methods. Alternatively, the conveyor belt shown in FIG. 1 may be inverted so that the vacuum system 110 applies suction from above. In such a configuration, the fabric 125 is carried over a supply of SAP particles 135 and the SAP particles are held onto the surface of fabric 125 by vacuum system 110. In alternative embodiments, SAP dispenser 130 may include skin care particles such as ion exchange resins, deodorant, anti-microbial agents, binder particles, or other beneficial particles. Further, although the preferred embodiment is directed to SAP particles, the methods discloses herein can be used with any combination of the above referenced particles, including combinations that do not include SAP. Alternatively, separate dispensers advantageously positioned along the production line (not shown) may be used to deposit different types of particles such as, for example, skin care particles.

The SAP particles 135 are positioned and concentrated on the fabric 125 according to a number of alternative methods. In one embodiment, the vacuum system 110 and fabric 125 may be configured to allow the vacuum system 110 to pull the SAP particles 135 against the surface of the fabric 125 uniformly or in particular areas. In another embodiment, the shape of the fabric 125 guides the SAP particles 135 into position. For example, when the fabric 125 is shaped to form pockets, the SAP particles 135 roll into the pockets as a result of the vacuum system 110, the vibration of the conveyor belt, air flow, the angle of the conveyor belt, or combinations thereof. Alternatively, the SAP dispenser(s) 130 may be positioned and controlled to dispense SAP particles 135 strategically across the surface of fabric 125, which strategic positioning includes but is not limited to alignment or nonalignment with the machine direction, offset, or randomly. Further, SAP may be positioned such that there are zones without SAP particles. Still further, SAP particles may be positioned using adhesive such as by applying adhesive to specific locations on a surface, depositing SAP particles on the surface. Still further, SAP particles may be positioned on both fabrics 125 and 155.

Once SAP particles have been deposited and positioned on fabric 125, a second fabric 155 is introduced into the production line from roll 150. The second fabric 155 may be selected from a variety of materials including spun-bonded thermoplastic or similar woven or nonwoven material, film, or combinations thereof.

The adhesive 145 is applied to the SAP particles 135 in a number of ways. FIG. 1 shows the adhesive 145 applied to the fabric 155. Alternatively, the adhesive 145 may be applied to the fabric 125 and SAP particles 135, fabric 125 before the SAP particles 135 are deposited on the fabric 125, or directly to the SAP particles before they are deposited on the fabric 125. In still another embodiment, the adhesive 145 is applied at the point where fabrics 125 and 155 are jointed together. In still another embodiment, multiple coats of adhesive are applied. For example, adhesive 145 may be applied to the fabric 125 before the SAP particles 135 are deposited, to the SAP particles 135 after they have been positioned, to the fabric 155, or a combination thereof. Alternatively or in addition to the above embodiments, binder particles may be mixed with the SAP particles 135. Additionally, the adhesive may be applied uniformly, randomly, or in a specific pattern, depending the desired absorbent properties of the finished composite.

The adhesive is applied according to a number of methods know to those skilled in the art. For example, the adhesive may be sprayed, rolled, or spun onto the surface of fabric 155. The adhesive may be hydrophobic, hydrophilic, biodegradable, bioderived, or combinations thereof. The preferred adhesive is hydrophilic. The concentration of adhesive in a coat varies between 0.5 and 100 grams per square meter ("GSM"). Optimally, the concentration is between 1 and 25 GSM. In a preferred embodiment, the concentration is between 2 and 10 GSM. Additionally, enough adhesive should be applied to cover at least 25% of the targeted area.

Fabrics 125 and 155 are then bonded together. FIG. 1 shows a thermal bonding system in which calendar rolls 160 and 170 are used. However, other bonding systems/methods may be used. For example, the ultrasonic bonding system of FIGS. 4 and 5 may be used. Adhesive 145 retains the SAP particles 135 in a relatively fixed position with respect to the fabrics during the bonding process and subsequent to the bonding process. The bond pattern may be aligned with the distribution of the SAP particles 135. Alternatively, the bond pattern may not be aligned with the distribution of the SAP particles 135. In such embodiments, the bonding equipment may be adapted to nudge the SAP particles 135 aside prior to bonding or to bond through the SAP particles 135. These embodiments eliminate the need to synchronize the bond points with the distribution of SAP particles.

Fabrics 155 and 125 are shown as two materials. However, one skilled in the art understands that the fabrics may actually be part of the same material. In such a configuration, the unitary fabric is folded to cover the SAP particles. Alternatively, the edges of fabric 125 may be folded prior to applying the second fabric 155. In embodiments in which fabrics 125 and 155 are separate, fabrics 125 and 155 may be the same or a different material. Additionally, fabric 155 may be sized to cover specific areas, such as the center section, of fabric 125.

Once the fabrics have been bonded together, the absorbent composite 195 is collected on rewinder 200.

Figure 2:
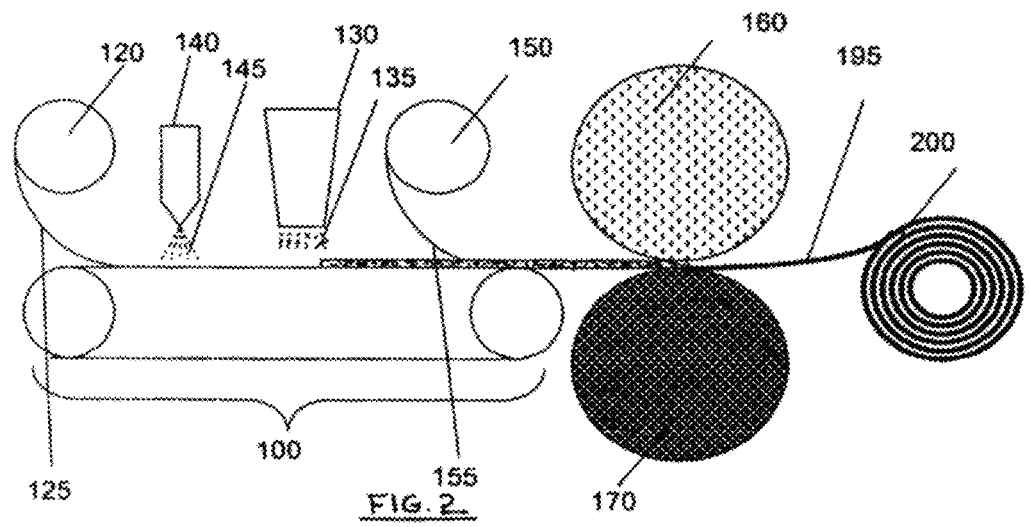
FIG. 2 is a schematic of another embodiment of a method of making the inventive absorbent composite using calendar rolls.

In a method illustrated in FIG. 2, the fabric 125 is transported along the conveyer belt 100. As fabric 125 is transported along the conveyer belt 100, a thin coat of adhesive 145 is applied to fabric 125. As with the method of FIG. 1, the adhesive may be applied uniformly, randomly, or in a specific pattern, depending the desired absorbent properties of the finished composite. Although the adhesive 145 is shown being applied before the SAP Particles 135 are deposited, alternate embodiments are envisioned. For example, the adhesive may be applied according to the embodiments described with respect to FIG. 1.

Following the application of the adhesive, SAP particles 135 are deposited and positioned on the fabric 125. The SAP particles 135 may be deposited directly on fabric 125, as shown in FIG. 2, or indirectly, such as by air flow blowing SAP particles across fabric 125. The weight of the SAP particles aids in securing the fabric 125 to the conveyor belt 100. Additionally, the SAP particles may be positioned in a manner similar to that disclosed for FIG. 1.

A second fabric 155 is then fed into the production line from roll 150. The second fabric is positioned to cover the SAP particles 135. The adhesive 145 prevents the SAP particles from moving freely between the two fabrics. The resulting sandwiched construction is then transported to the calendar rolls for thermal bonding. As described with respect to FIG. 1, the bond pattern may be aligned or not aligned with the SAP particles 135. The absorbent composite 195 is then collected by rewinder 200. As described with respect to FIG. 1, fabrics 125 and 155 may be part of a single sheet. Additionally, the fabrics may be folded in the manner described for FIG. 1. In another embodiment, the fabric 125 may be coated with adhesive and pressed on a supply of SAP particles.

Figure 3:
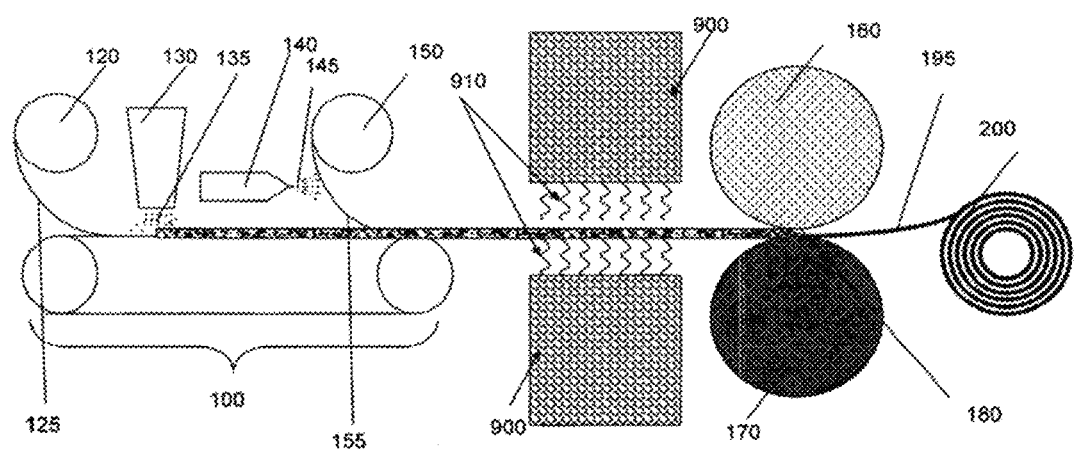
FIG. 3 is a schematic of the method shown in FIG. 1 with an additional energy source.

FIG. 3 is similar to FIGS. 1 and 2, except that an energy source 900 such as an oven or microwave generator is positioned along the assembly line. The energy source applies heat and or radiation 910 that can be used to melt thermal plastic binder. The amount of heat may also be regulated to melt specific types of particles or fibers, specific sections of the fabrics, or only the outer layers of particles/binder.

Figure 4:
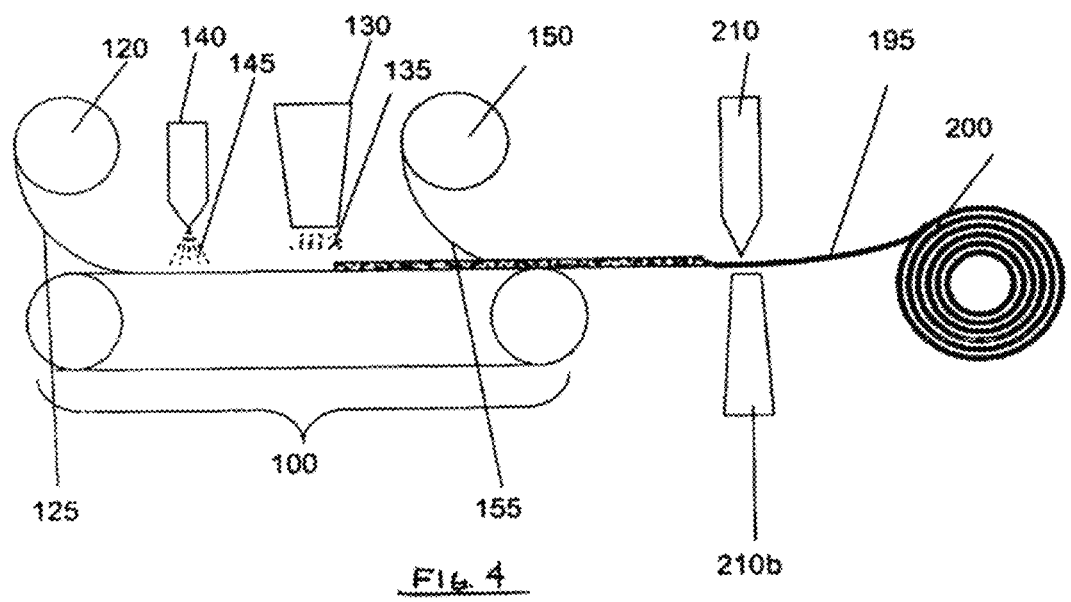
FIG. 4 is a variation of the method shown in FIG. 1 that uses ultrasonic bonding techniques instead of calendar rolls.
Figure 6A:
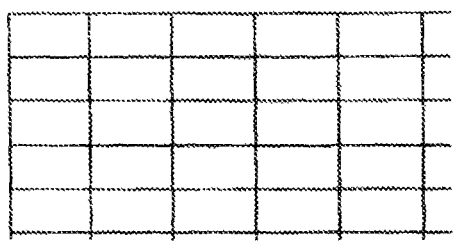
FIGS. 6A-6Q are illustrations of various potential bonding patterns that may be used in the method and absorbent article.
Figure 6B:
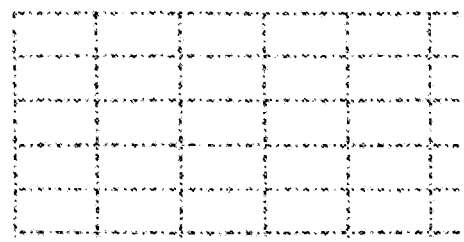
Figure 6C:
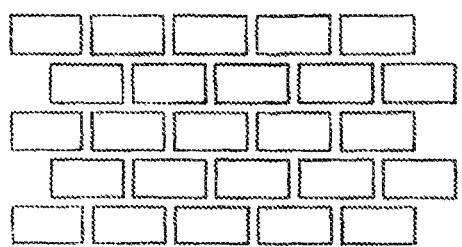
Figure 6D:
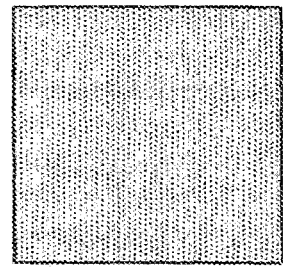
Figure 6E:
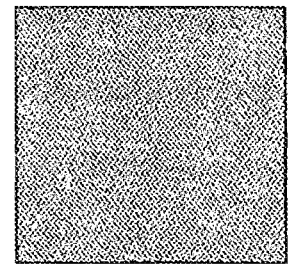
Figure 6F:
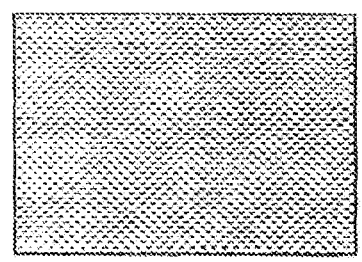
Figure 6G:
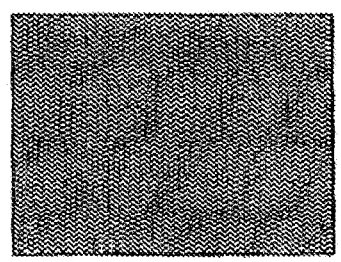
Figure 6H:
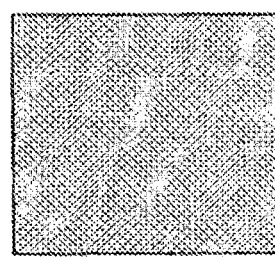
Figure 6I:
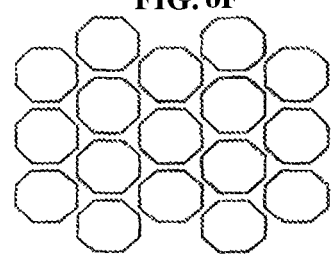
Figure 6J:
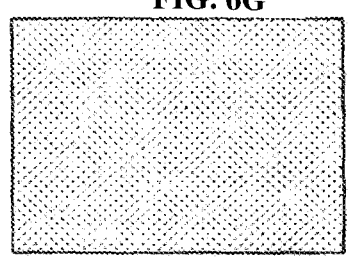
Figure 6K:
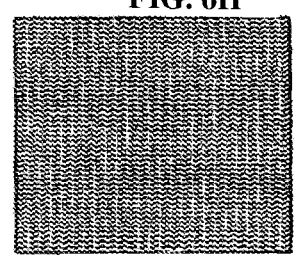

FIGS. 4 and 5 are similar to FIGS. 1 and 2, except that the fabrics are bonded together using ultrasonic bonds. FIGS. 4 and 5 show an ultrasonic bonding system (210*a* and 210*b*). It is readily understood that FIGS. 1-5 show different embodiments of the novel method and that aspects of the various methods may be advantageously combined depending on the need. Important to all combinations, however, is the amount of adhesive 145, binder particles, or combinations thereof applied to the SAP particles 135 and the strength of the bonds. As noted with respect to FIG. 1, the optimal concentration of adhesive is between 12 and 50 GSM, though other concentrations are acceptable. In all embodiments, it is important that the concentration of adhesive 145 be high enough to inhibit the migration of SAP particles 135. The concentration should not be so high, however, that it coats the SAP particles 135 and reduces SAP swelling. The adhesive should only inhibits the migration of enough SAP particles 135 to assure uniform absorbency. Although not shown, one skilled in the art understands that the energy source 900 shown in FIG. 3 can also be applied in the configurations shown in FIGS. 2, 4 and 5.

FIG. 6 (*a*) through (*q*) show various bonding patterns contemplated by the method. The bonding patterns may completely enclose an area, partially enclose an area, or provide local bonding zones. The lines and points indicate the bond sites. The solid lines depict bond lines. The bond lines may form open shapes or enclosed shapes, such as can be found in examples (a) and (c), which depict continuous bond lines that completely enclose pockets of SAP particles 135 or, as in example (g), separate distinct regions of the absorbent composite. The dashed lines, such as can be found in examples (b) and (m), are discontinuous bond patters that do not completely enclose pockets of SAP particles 135. In these configurations, the migration of dry SAP particles is inhibited by the adhesive and continuous or discontinuous bond patters. Discontinuous pond patters may be substituted for continuous bond patterns and vise versa. Further, though the FIG. 6 shows either continuous or discontinuous bond patters, combinations of discontinuous and continuous bond patters may be used.

Figure 7:
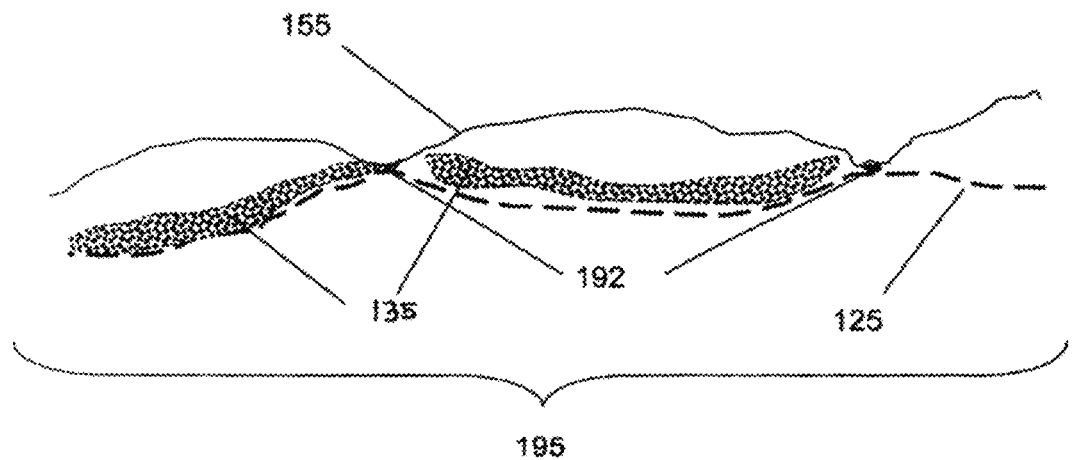
FIG. 7 is a cross sectional illustration of a pockets formed by the method and utilized in the absorbent article.

FIG. 7 shows a partial cross-section of an absorbent composite 195. FIG. 7 shows how bonds 192 may act to separate pockets of SAP particles 135. As noted with respect to the bonding pattern, SAP particles 135 may be entirely enclosed in pockets defined by the bonding pattern, partially enclosed in pockets defined by the bonding pattern or merely inhibited by the bonding pattern. Inhibited in this context means the SAP particles 135 cannot move directly from one area of the core to another area, but instead, must move around bond sites.

Notably, multiple functions or advantageous properties are obtained in the absorbent composite by varying the amount of SAP particles, the type and number of fabrics used, and construction variables such as, the ratio of SAP to adhesive, and applying the absorbent composite at various locations in the article. Such manufacturing and design techniques may be incorporated into structural designs and methods of the present disclosure.

Additionally, one skilled in the art understands that the process for constructing a single absorbent composite described above may be modified to produce a multiple, laminated absorbent composite. In structures comprising multiple layers, the layers may be sheets of absorbent composite 195 that are laminated together to form a single structure or alternating layers of fabric and SAP particles 135 that form a single structure. One skilled in the art understands that alternating layers may be achieved by applying adhesive to the top of fabric 155 (FIG. 1), applying a second layer of SAP particles 135, and a third fabric (not shown). Similarly, additionally layers may be added, limited only by the maximum thickness suitable for the bonding process.

The SAP particles 135 may be coated with a miscible, hydrophobic material. The coating acts as a barrier or membrane that initially slows the liquid uptake, thereby saving SAP capacity for additional or secondary discharges. In this regard, the coating evens out the absorbency rates between discharges. In the processes shown in FIGS. 1 to 5, the coating may be applied prior to the adhesive 145 being applied, after the adhesive 145 is applied, or at the same time. Alternatively, the adhesive may be mixed with the coating material.

In one example, a light coating of mineral oil is applied over the SAP particles 135. The coating retards the initial uptake by the SAP particles and allows more time for the liquid to spread out in the article. Preferably, the mineral oil is applied at a concentration of about 0.00001 grams per gram of SAP to about 0.1 grams per gram of SAP (depending on the particular product design). Alternatively, the mineral oil may be applied in specific target zones. In this way, the received liquid is encouraged to initially spread to uncoated areas before the coated areas are activated and begin to swell.

An absorbent composite manufactured by the above-described process may be used for a disposable absorbent article or as one or more of the components of a disposable absorbent article. The components of an absorbent article include the backsheet, topsheet, absorbent core, containment walls or cuffs (including leg gathers), backsheet/absorbent core composite, topsheet/absorbent composite, and combinations thereof. Such constructions are described below in more detail.

Figure 8:
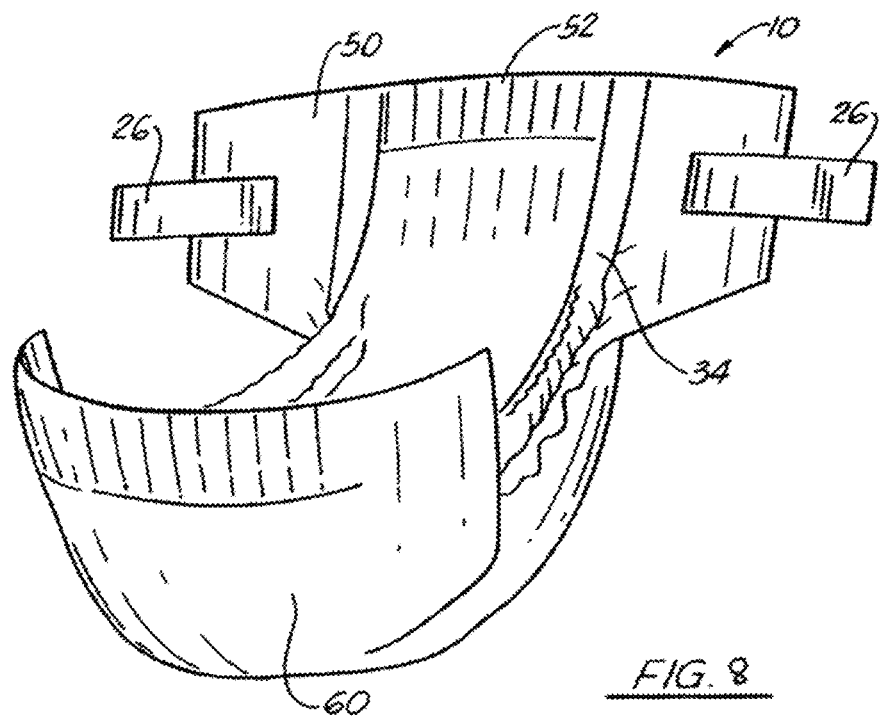
FIG. 8 is a perspective view of a disposable absorbent article embodying the absorbent composite.

FIG. 8 is a perspective view of a disposable absorbent article in the form of a diaper 10. Diaper 10 comprises a topsheet 50, a backsheet 60, and an absorbent core (not shown). The diaper further comprises upstanding barrier cuffs 34 which extend longitudinally along the diaper and are elasticized to conform to the buttocks of the wearer. Additionally, the diaper includes an elastic band 52 and fastening elements 26. Element 26, in use, extends to and engages the corresponding opposing end of the diaper to secure the diaper about the wearer.

Figure 9:
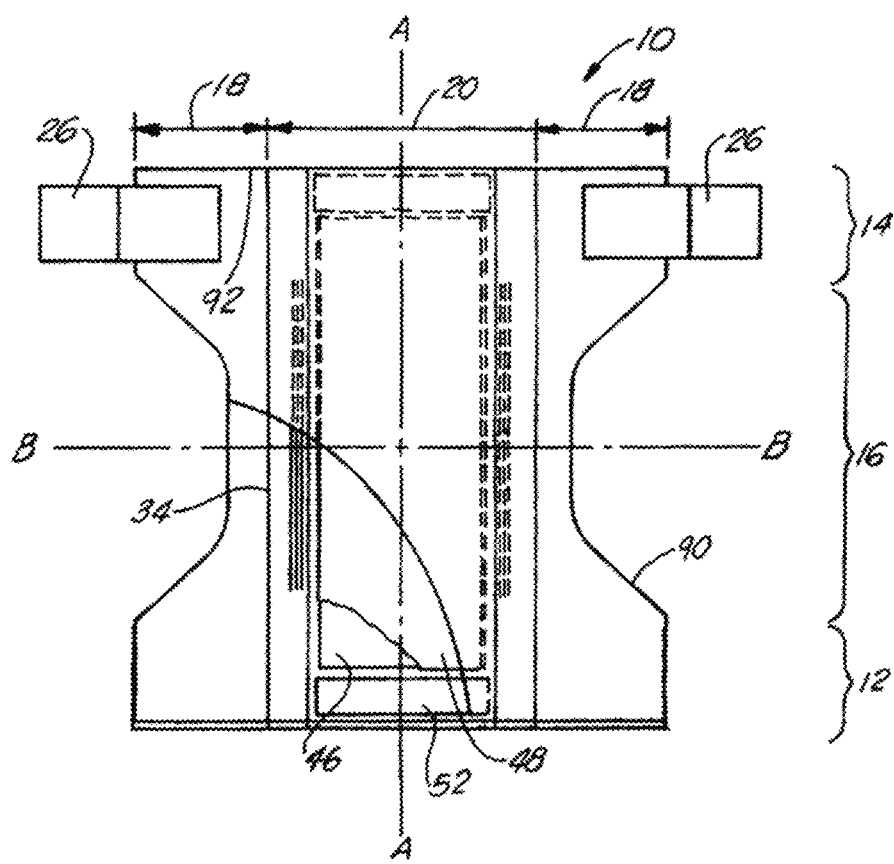
FIG. 9 is a top plan view of the disposable absorbent article of FIG. 8 in a flat and extended condition.

FIG. 9 illustrates a composite web structure of the diaper 10 of FIG. 8 in a generally flat and unfolded configuration. As will be explained further below, the web structure may be subsequently trimmed, folded, sealed, welded and/or otherwise manipulated to form a disposable diaper 10 in a finished or final form. To facilitate description of the diaper 10, the description refers to a longitudinally extending axis AA, a laterally extending central axis BB, a pair of longitudinally extending side edges 90, and a pair of end edges 92 which extend between side edges 90. Along the longitudinal axis AA, the diaper 10 includes a first end region or front waist region 12, a second end region or back waist region 14, and a crotch region 16 disposed therebetween. Each of the front and back waist regions 12, 14 is characterized by a pair of ear regions or ears 18, which are located on either side of a central body portion 20 and extend laterally from the side edges 90. A fastening structure 26 (e.g., a conventional tape fastener) is affixed to each of the ears 18 along the back waist region 14 of diaper 10.

When the diaper 10 is worn about the waist, the front waist region 12 is fitted adjacent the front waist area of the wearer, the back waist region 14 is fitted adjacent the back waist area, and the crotch region 16 fits about and underneath the crotch area. To properly secure the diaper 10 to the wearer, the ears 18 of the back waist region 14 are brought around the waist of the wearer and toward the front and into alignment with the ears 18 of the front waist region 12. The securing surface may be located on or provided by the interior or exterior surface of the front waist region 12. Alternatively, the fasteners 26 may be located on the ears 18 of the front waist region 12 and made securable to the ears 18 of the back waist region 14.

Figure 10:
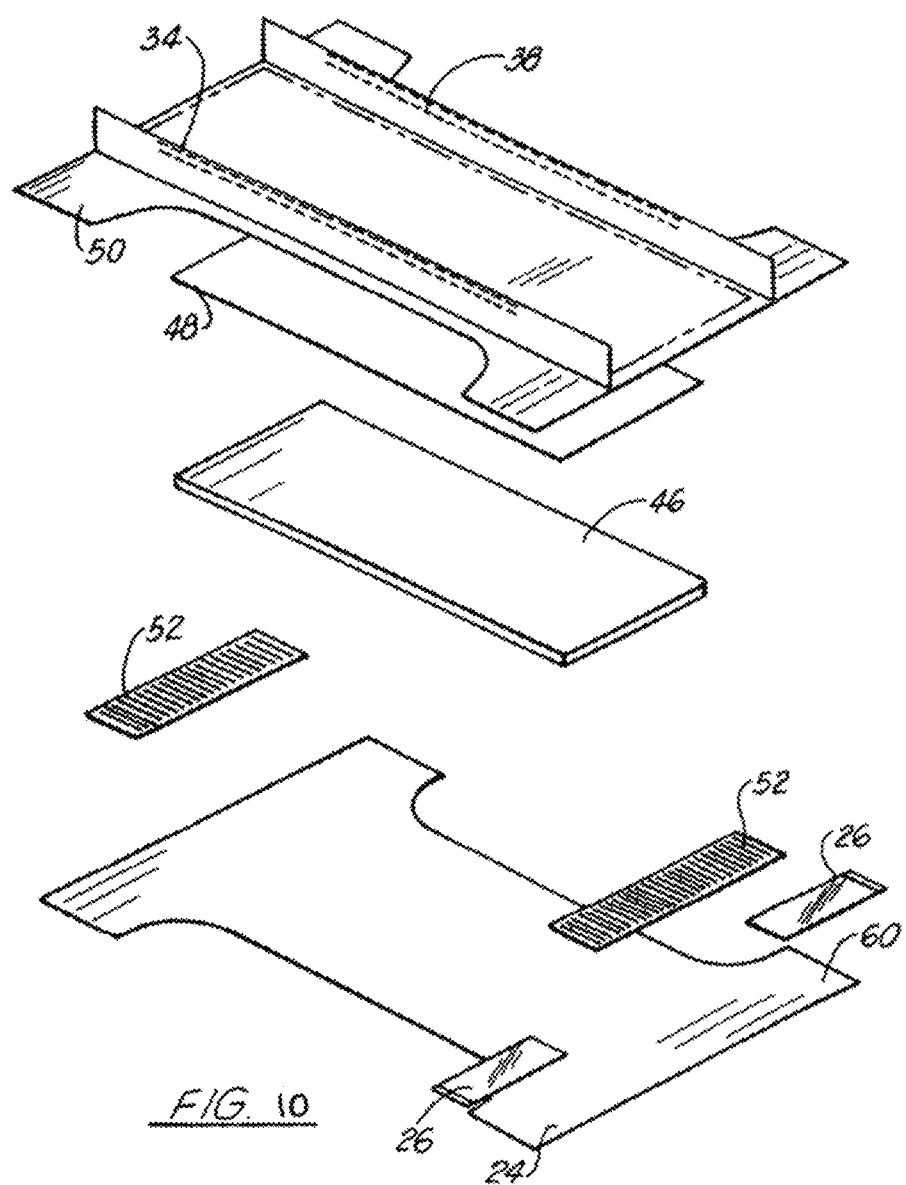
FIG. 10 is an exploded view of the disposable article of FIG. 8.

FIG. 10 is an exploded view of the diaper of FIGS. 8 and 9. A suitable diaper structure typically employs at least three layers. These three layers include a backsheet 60, an absorbent core 46, and a topsheet 50. The diaper structure mayor may not contain a pair of containment walls or leg cuffs 34 disposed upwardly from the topsheet 50 and preferably equipped at least with one or more spaced apart, longitudinally elastic members 38. It will be shown below that any of these diaper elements or a combination of these elements may be constructed with or using the absorbent composite 195. Additionally, an acquisition layer 48 could be added to improve performance.

Backsheet

As mentioned above, the diaper 10 employs a backsheet 60 that covers the core 46 and preferably extends beyond the core 46 toward the side edges 90 and end edges 92 of the diaper 10. In one aspect of the invention, the backsheet 60 is constructed from a single-layered material sheet of absorbent composite 195. In such a configuration, fabric 125 is positioned as an outer surface of the backsheet 60.

Additionally, an alternative structure could be used for gel blocking. For an application using gel blocking, a backsheet of the inventive disposable absorbent article is relatively thin and provides improved flexibility. When dry, the backsheet is soft and breathable, but upon wetting, a thin, gel blocked layer is formed (i.e., on the inner surface of the backsheet) which renders the backsheet substantially liquid impervious. The gel blocked layer is formed by the swelling of the SAP particles 135.

Topsheet

Similarly, the absorbent composite 195 may be utilized with or as the topsheet of an absorbent garment. The topsheet 50 is preferably soft, compliant, exhibits good strikethrough and a reduced tendency to rewet from a liquid pervious material. The topsheet 50 is placed in close proximity to the skin of the wearer when the diaper 10 is worn. In this way, such a topsheet 50 permits bodily discharges to rapidly penetrate it so as to flow toward the core 46 more quickly, but not allowing such discharges to flow back through the topsheet 50. The topsheet 50 may be constructed from anyone of a wide range of liquid and vapor permeable hydrophilic materials. The surface(s) of the topsheet may be treated with a surfactant so as to facilitate liquid transfer therethrough, especially at a central zone or area of the topsheet located over the core and an inner surface of the core. The topsheet may also be coated with a substance having rash preventing or rash reducing properties (e.g., aloe vera).

In one example, the topsheet 50 is formed from an absorbent composite 195 that covers substantially the entire area of the disposal absorbent article 10, including substantially all of the front waist region 12, back waist region 14, and crotch region 16. Further, the ear layer of the inner region 18 is formed from the same single topsheet material and, thus, may be referred to as being unitary with the topsheet 50 in forming lateral extensions of the topsheet material. Alternatively, the topsheet 50 may be formed from multiple different materials which vary across the width of the topsheet 50. Such a multiple piece design allows for creation of preferred properties and different zones of the topsheet.

Absorbent Core

Figure 11:
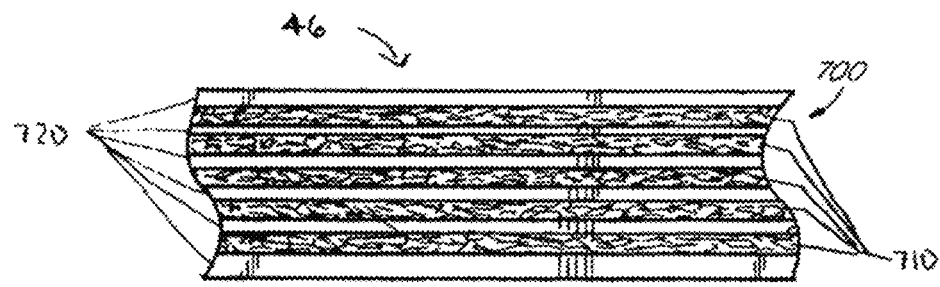
FIG. 11 is a partial cross-sectional view of an absorbent core utilizing the absorbent composite and employed by an absorbent article.
Figure 12:
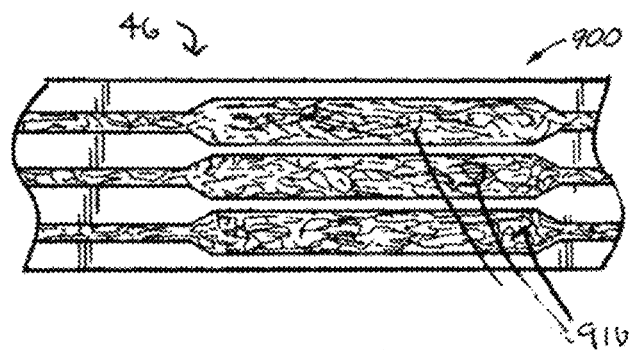
FIG. 12 is partial cross-sectional view of an absorbent core utilizing an alternative embodiment of the inventive absorbent composite and employed by an alternative absorbent article.

In addition to or as an alternative to the above examples, the absorbent core of the disposable absorbent article may be constructed from the absorbent composite 195, laminated layers of absorbent composite 195 (not shown) or multiple layers of SAP particles 135 and fabric. FIGS. 11 and 12 depict cross sectional views of alternating layers of SAP particles 135 and fabric that form a multi layered absorbent composite 700 and 900, respectively. As shown in these drawings, the core 46 may be comprised of distinct layers of SAP particles 135 (710 and 910). The layers may be uniform or non-uniform, depending on the intended application. In the non-uniform multi layered absorbent composite 900, the concentration of SAP particles 135 may vary within a given layer, between layers, or combinations thereof.

FIG. 11 depicts a composite structure 700 in which SAP particle layers 710 and fabric layers 720 are alternated to form the completed composite structure 700. The layered design can also be constructed by bonding together sheets of absorbent composite, folding a unitary sheet of absorbent composite, or constructing absorbent composites with multiple layers during the manufacturing process. In folded applications, the composite fold may be a C-fold, Z-fold, V-fold, W-fold or combinations thereof. Further, the folds may be open, closed, or overlapping.

FIG. 12 depicts multi layers absorbent composite 900. As shown in FIG. 12, high concentrations areas of SAP particles 910 may be strategically positioned to provide additional absorbency in specific regions such as the crotch of an absorbent article. One skilled in the art understands that the high concentration areas may be offset to control the amount and direction of liquid penetration. Additionally, the layer with zones of high concentrations may be combined with layers of substantially uniform layers. Alternatively, the high SAP concentration areas can be formed by positioning multiple layers of absorbent core.

The core may be configured to extend substantially the full length and/or width of the disposable absorbent article. Preferably, however, the core is disposed or is otherwise concentrated at the crotch region of the article. In various embodiments, the core extends to the edges of the article and the SAP particles 135 are concentrated in the crotch region or another target zone of the article. In still another embodiment, the particles can be a combination of SAP particles, skin care particles such as ion exchange resins, deodorant, anti-microbial agents, binder particles, or other beneficial particles.

Containment Walls

Figure 13:
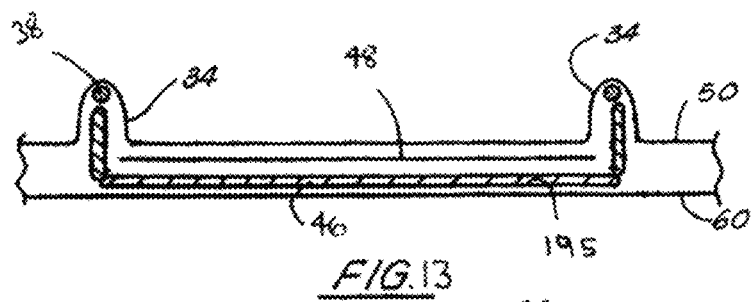
FIG. 13 is a cross-sectional view of an absorbent article employing in the leg cuffs an absorbent composite.
Figure 14:
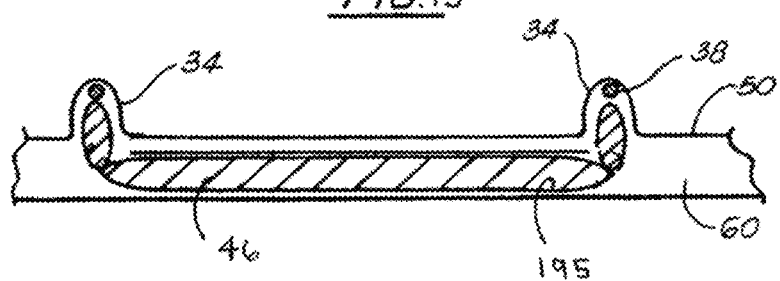
FIG. 14 is a cross-sectional view of an absorbent article employing in the leg cuffs a saturated absorbent composite.

Now turning to FIGS. 13 and 14, the disposable absorbent article 10 utilizes a pair of containment walls or cuffs 34 which employ the absorbent composite 195. Each containment wall 34 is a longitudinally extending wall structure preferably positioned on each side of the core 46 and spaced laterally from the longitudinal center. The longitudinal ends of the walls 34 may be attached, for example, to the topsheet 50 in the front and rear waist regions 12 and 14. Preferably, the ends of the containment wall 34 are tacked down inwardly and attached, for example, by adhesive to the web structure. Such a construction effectively biases the containment wall 34 inwardly and is generally considered to cause containment wall 34 to exhibit improved leakage prevention properties.

FIG. 13 provides a cross-sectional view of a diaper 10. The diaper 10 includes backsheet 60, absorbent core 46, acquisition layer 48, and topsheet 50. As shown in FIG. 13, the core is an absorbent composite 195. The diaper 10 also includes a pair of containment walls or cuffs 34 which are formed by folding the topsheet 50 and wrapping it about the ends of the absorbent composite 195. Alternatively, the absorbent composite 195 in the cuffs 34 may be distinct from the absorbent core 46.

Preferably, the containment walls 34 are equipped with elastic members 38, which extend along a substantial length of the containment walls 34. In a common application, the elastic members 38 are placed within the containment walls 34, preferably at the top of the containment walls 34 while in a stretched condition and the glued to the containment walls at least at their ends. When released or otherwise allowed relaxing, the elastic members 38 retract inwardly. When the article 10 is worn, the elastic members 38 function to contract the containment walls 34 about the buttocks and the thighs of the user in a manner, which effects a seal between the article 10, the buttocks and the thighs. The core 46 may be a single sheet of absorbent composite 195 or multilayered, as described above.

FIG. 13 depicts the configuration of the containment walls 34 when it is soft and dry. FIG. 14, on the other hand, depicts the containment walls after wetting, in which the absorbent composite 195 has swollen to dispose the containment walls 34 in a resiliently, erect position. Unlike traditional leg cuffs in the prior art, the resiliently erect containment walls 34 resists flattening (e.g., when the wearer sits down) and, thereby, ensures leakage prevention, especially of explosive, liquefied bowel movements and rapid discharges of urine.

Optional Layers

The disposable absorbent article may employ additional layers including an acquisition layer or surge layer 48, preferably situated between the topsheet and the core (e.g., FIG. 10). One function of such an acquisition layer is to spread out or disperse liquid flow so that liquid is distributed more evenly over the core surface. This serves to slow down the flow so that the liquid has adequate time to be absorbed by the core. The acquisition layer also serves to prevent the core from being saturated locally, while a substantial remainder of the core is not absorbing any liquid.

Tape Tabs

The disposable absorbent article must be secured to the wearer. This is most important with respect to diapers since diapers are not pulled up by the wearer, like training pants or incontinent briefs, but are fastened around the wearer. Securing elements compliment the elastic members by effecting a quasi-seal between the wearer and the waistband and leg cuffs, so that liquid is contained within the article which is then absorbed; in other words, so that it does not leak through gaps between the wearer and the edge of the article. The securing elements may be adhesive, mechanical fasteners hook and loop features, or conceivably strings, i.e., anything that will secure one end of the article to the longitudinally opposite end. The securing elements may also be co-adhesive such that they adhere to each other but not other materials.

In the examples shown in the Figures (see, e.g., FIG. 10), the article 10 is affixed to the wearer by tape fasteners 26 which are permanently affixed to (e.g., sewn directly into) the backsheet 60. Tape fasteners 26 are contacted with the transversely opposite ear 22 extending from the backsheet, where they remain affixed due to adhesive compound applied to the fasteners 26. Alternatively, the article 10 may be training pants, pull-on diapers, and the like. In this configuration, the article 10 mayor may not have tape fasteners 26.

Waistband

Waistbands employing elastic members 52 are positioned along the transverse portion of the article 10 so that when worn, the waistbands are positioned along the waist of the wearer. Generally, the waistband preferably creates a quasi-seal against the waist (transverse elastic members 52) so that liquid waste does not leak from the regions between the waist elastic and the waist of the wearer. The quasi-seal is significant because, although the liquid may be eventually absorbed by filler material, the assault of liquid by the wearer may overwhelm the absorption rate capacity of the filler material. Hence, the waistbands contain the liquid while it is being absorbed. Secondly, the waistbands may have a capacity to absorb liquid (see, e.g., U.S. Pat. No. 5,601,544, which is hereby incorporated by reference).

Aggregate (and Embossing) Patterns and Material Selection for Fluffless Absorbent Composites The simplified illustrations of FIGS. 15A-15D present absorbent composites 510 with particularly advantageous arrangements of aggregates 512 of absorbent particles, according to the present disclosure (with like reference numerals used to indicate like elements). Referring first to FIG. 15A, each of the aggregates on the absorbent composite 510 is represented by the diamond-shaped enclosure 514 in the pattern. In preferred embodiments, SAP is employed as the absorbent particles in the aggregates. Furthermore, SAP aggregates in each of FIGS. 15A-15D are preferably maintained in place and stabilized by physical entrapments or containers provided by the engagement of a first fabric disposed generally above the SAP aggregate with a second fabric disposed generally beneath the SAP aggregate. Thus, in an alternative view of FIG. 15A, the diamond units represent the outline of the containers or pockets, reflecting in particular embodiments, the engagement of the top fabric with the bottom fabric, as previously described herein.

As described previously, the absorbent performance of the SAP can be affected by the size and structure of the container. As SAP becomes more saturated, its permeability is reduced. Water cannot pass through the SAP particle due to the high level of water already contained within the SAP particle and eventually the SAP can completely halt the passage of further fluid through it. This is known as gel blocking. Also, as SAP becomes more saturated, it swells and its volume increases. By confining the SAP in a small container of fixed volume it is possible to restrict the swelling of the SAP and prevent it from reaching its highest saturation levels (and, by consequence, stop the SAP from reaching its lowest levels of permeability). The degree to which the SAP particle is restricted depends on a number of factors, including: the nature and size of the container, the size and frequency of any breaks in the container (e.g., along the side walls), the amount of SAP disposed in the container, and the amount of fluid absorbed by the SAP. Further, the performance properties of SAP are affected by its degree of saturation. Specifically, absorbent composite properties such as permeability, absorption rate, capillary pressure (arising from the void space in the composite) will vary significantly as the SAP changes from dry to fully saturated. In accordance with a method of the present disclosure, target or optimal performance of the SAP may be achieved by changing the size of the container and/or the SAP concentration so as to physically constrain the swelling of the SAP and limit the maximum saturation point of the SAP. By incorporating these physical features, preferred levels of permeability or a preferred absorption property may be achieved in target regions of the absorbent core. Thus, by playing with the two variables of pocket size and the amount of SAP in the pocket, the minimum permeability of that container or pocket may be "set". Pockets in some regions of the diaper may be prevented from gel blocking and the permeability of that region of the core may be optimized. A gradient of pocket size may also be established to obtain maximum flow and utilization of the absorbent core. This gradient will be radiate from the target zone towards the ends or sides of the diaper.

The various arrangements of containers or pockets also promote SAP and core utilization and prevent fluid from bypassing the containers. Ideally, fluid should leak or flow from container to container as the SAP reaches the optimum level of saturation which is set either by the properties of the SAP or the volume of the pocket into which it is expanding. Applicants contemplate that, in some of the previously described composites or arrangements of pockets (see FIG. 6), there may be a tendency for fluid to leak between the pockets. That is the fluid runs along the channels formed by embossing lines and does not enter the core. To mitigate this tendency, arrangements or patterns for the containers are preferably ones that minimize or eliminate short and direct routes (as may be established along embossing lines) of fluid flow from the core center to the side margins of the core (at end edges). To illustrate, containers or pockets shaped as diamonds are preferred to ones formed in squares or rectangles, because the diagonal lines or channels formed by the diamond containers are longer and more circuitous. Circles are also effective if packed in a way that does not present channels that flow quickly to the edge. In more preferred arrangements, fluid flow is forced to change directions one or more times before flowing through the side of the diaper.

An absorbent core for a baby diaper or adult incontinence product is required to absorb fluid quickly, in an anatomically aligned region of the core, absorb all the fluid without leaking at the sides or ends of the product and hold on to that fluid without wetting the user's skin particularly when under the pressure caused by the user's bodyweight. This present disclosure accomplishes that by providing regions of the core having different performance parameters defined by the size of the containers retaining the SAP, as well as the arrangement of the containers. Thus, a core may be designed to attain optimized performance characteristics by changing the size of the pocket and/or the concentration of SAP within that pocket.

In certain arrangements shown here, design features are combined to provide a core that is less likely to leak, absorbs wetness fast, and provides a dry, comfortable feeling for the user. At the crotch region of the core, the container size and SAP loading are optimized to provide an open structure, with high permeability, resulting in fast acquisition or distribution of fluid away from the point of insult and away from the user's skin. Permeability is maintained even when the SAP is swollen due to the physical constraints of the container restricting further swelling. This allows the liquid to spread more efficiently toward the regions further away from the target zone (crotch area), and contributes to better performance and utilization of the absorbent core. At regions away from the crotch region, such as regions proximate the periphery of the core and beyond, permeability is reduced to slow down the fluid. Absorption capacity is increased by the larger pockets allowing the SAP to swell more fully and hold on to more fluid.

In FIG. 15A, large diamond shaped containers or pockets 514 of absorbent particles aggregate 522 are present in a region anatomically aligned with the point of insult. The containers then gradually reduce in size toward the sides and front and rear margins or edges of the core 510. There are three distinct regions of containers. In the crotch region "A", large diamond shaped pockets are provided. Adjacent and surrounding the crotch region is an intermediate region "B" of pockets of smaller size than those in the crotch region (A). Among other things, the smaller pockets of this intermediate region (B) present breaks in the potential fluid flow around the SAP aggregates and along embossing lines. As described previously, the presentation of such barriers to direct escape of fluid flow through the side margins prevents leakage and promote utilization of the SAP aggregates. Finally, a third region "C" of pockets is present near each of the end edges of the core 510 populated by even smaller sized pockets of SAP aggregates.

FIG. 15B illustrates a second exemplary arrangements of SAP aggregates 522 and pockets 514. In this example, small, diamond shaped pockets 522 are disposed in the region anatomically aligned with the point of fluid insults. The pockets then gradually increase in size in regions disposed toward the sides and front and rear edges of the core. The two arrangements (in FIGS. 15A and 15B) provide alternative ways of structuring the expected flow gradient and as well, handling of the liquid insults. The absorbent composite and arrangement of pockets in FIG. 15A may provide for a center region with a larger capacity initially, but which, over time, will redistribute liquid in its void volume, or from subsequent liquid insults, to smaller adjacent pockets or cells. With the pattern of FIG. 15B, the center region may be equipped with smaller capacity initially, which will cause the liquid to travel to larger cells. It may also generate a surface topography that prevents leakage from the sides and ends of the diaper, i.e., "dams" will be created that intercept and absorb surface flow.

FIGS. 15C and 15D provide alternate arrangements wherein circular pockets for SAP aggregates are employed. In FIG. 15C, large, circular shaped pockets are present in a region anatomically aligned with the point of insult. The pockets 534 gradually reduce in size toward the sides and front and rear edges of the core 530. The pattern is similar to that employed in FIG. 15A but with circular pockets rather than diamond-shaped ones. Many of the characteristics of the arrangement in FIG. 15A translate to the design of FIG. 15C.

However, unlike a diamond shaped pocket, it is not possible to produce a perfectly close packed pattern with circular shaped pockets and the resulting space between the circular pockets could be disposed in a number of ways. It is envisaged that the space between the circular pockets could either be completely embossed (i.e., have large embossed, thermally bonded regions between the pockets), partially embossed or not embossed. The spaces could also contain SAP or be free of SAP.

FIG. 15D illustrates a further embodiment of the present invention, with a pattern analogous to that found in FIG. 15B. In this example, small, circular shaped pockets 544 are disposed in the region anatomically aligned with the point of fluid insults. The pockets 544 gradually increase in size in regions disposed towards the sides and front and rear edges of the core. Again the space between the pockets 544 could be utilized in a number of ways as described above.

It should be noted that arrangements and embossed patterns are not limited to employment of diamond shaped pockets or circular shaped pockets. Other shapes are contemplated. Some arrangements may even utilize different pocket shapes within the same pattern.

The following table summarizes the characteristics of the different pocket sizes, assuming the SAP concentration remains uniform throughout the core.

TABLE 1

Summary of Performance by Product Size and degree of SAP Saturation

| SAP Saturation | Small | Pocket Size Medium | Large |
|---|---|---|---|
| Dry (0%) | | Very high permeability Moderate absorption rate High capacity remaining | |
| Low (10-20%) | High permeability High absorption rate Low capacity remaining | High permeability High absorption rate Moderate capacity remaining | High permeability High absorption rate High capacity remaining |
| Medium (20-60%) | High permeability No further absorption | High permeability Low absorption rate Low capacity remaining | High permeability High absorption rate Moderate capacity remaining |
| High (60%+) | — | Moderate permeability No further absorption | Low permeability Low absorption rate Low capacity remaining |

Systems, Method, and Structures for Absorbent Particles Construction and/or Stabilization In a further variation of providing an absorbent composite according to the present disclosure, one or more of the nonwoven webs employed in previous examples is replaced with a more open structure. Examples of such a nonwoven include, carded PET webs, airthrough bonded nonwovens, resin bonded nonwovens and non-absorbent air-laid structures. Materials known as acquisition and distribution layers (ADL) are included in this list of suitable materials. The resulting structure provides an alternative means for containing absorbent particles and more specifically, within a fibrous network but without using an absorbent matrix of fibers (i.e., without pulp). The structure promotes the distribution of the SAP within a network of fibers provided by the non-woven web layer. This distribution of SAP particles into the more open web provides, among other things, a mechanism for further stabilization of the SAP within the nonwoven simply through entanglement of the particles within the fibrous network.

Figure 16A:
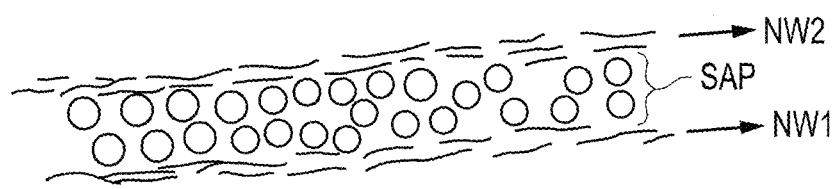
FIG. 16A is a simplified illustration of a prior art SAP sandwich.
Figure 16B:
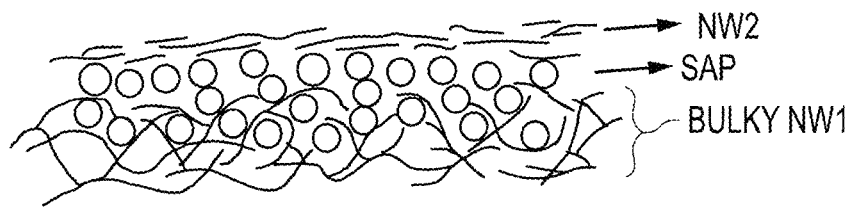
FIG. 16B is a simplified illustration of an SAP structure (sandwich) in accordance with the present disclosure.

FIG. 16A illustrates a composite structure as previously described. The composite employs a non-woven as a bottom layer (NW1) and a top layer (NW2) to sandwich a layer of SAP material (SAP). FIG. 16B illustrates an alternative structure, wherein a bulky non-woven ("bulky" NW1) is employed as a base layer. The bulky non-woven layer NW1 provides fibers that extend outward and entangle SAP particles. Such entanglement with the fibers in the more open material leads to stabilization of the SAP within the absor- bent composite. In a manufacturing process, SAP particles applied onto a sheet or web of the bulky woven may be energized so as to promote penetration into the fibrous network of the more open nonwoven web. The effect of gravity on the particles may be sufficient to promote the desired penetration as the SAP particles are laid down onto the web. Techniques such as vacuum or vibration could be used to further enhance the penetration of the SAP particles into the open, fibrous network.

Stabilization of the SAP prevents movement of the material during processing, storage and use. In exemplary embodiments, the absorbent composite or core may employ the "bulky nonwoven" structure (as in FIG. 16B) for stabilizing the SAP in addition to the use of adhesive and containers or pockets of SAP aggregates, as previously described.

It should also be noted that the more open nonwoven material can provide additional performance features. These include faster acquisition of fluid and improved dryness (rewet) for the user. Also, the absorbent matrix will feel softer (spongier) than "flat" nonwoven webs, and will provide a more flexible composite. This results in greater comfort for the user and a better fit around the contours of the user's body leading to less chance of leakage.

Referring now to the illustrations in FIGS. 17A-17B, the exemplary absorbent composite is preferably provided with top layer of "bulky" nonwoven. The illustrations may be regarded as simplified cross-sectional views of the composite in FIG. 15A. Because the substrate used to contain the SAP is an open structure nonwoven, it is characterized by large pores (~2000 microns). Embossing will set and stabilize the local pore structure of the bulky, resilient fiber web substrate. Areas wherein the embossing pattern is small (utilizes small containers) (FIG. 17A) creates smaller pores (see FIG. 17A) compared to areas with larger embossing patterns (FIG. 17B) which creates larger capillary pores (17B). In other words, the smaller inter-fiber distance characterized by the smaller patterns lead to higher densities and higher capillarity. The larger patterns provide greater inter-fiber distances which lead to low density and low capillarity. The result of this combination of pockets across the core is an optimized wicking structure, as illustrated in FIG. 17C. With larger pores situated in the target area and smaller pores away from the insult point, an effective conduit for fluid flow results. This conduit may be utilized to transport liquid against gravity more efficiently. (See illustration of liquid movement in FIG. 17c). Such an advantageous structure can be created within the nonwoven substrate by the appropriate choice of embossing patterns hence allowing the liquid to spread further, enhancing core utilization and intake.

In further embodiments and in reference to FIGS. 17C and 17D, 3-D patterns or contours may be formed during use (uptake of liquid) as a consequence of SAP swelling. As shown in FIGS. 17C and 17D, different size pockets provide differences in swelling capacities, which in turn lead to differential swelling. In one respect, dams may be created by the pockets with greater swells (i.e., larger pillows). This structural consequence helps to reduce side and waist leakage. In most cases, uncontrolled liquid (liquid pooling on the surface of the product) lead to product leakage. The 3-D topography generated as SAP swells is defined by the embossing pattern size/frequency. An absorbent core that can self-generate a surface topography can inhibit cross-directional surface flow (to prevent side leakage) or discourage leakage at the waist region (longitudinal ends of the core). The structure and arrangement of pockets in FIG. 15A would be well suited to achieve these properties in an absorbent core.

Further Exemplary Methods and Systems for Making an Absorbent Composite Employing SAP In a method referred to as profiling, the SAP dosing rate is varied to produce a profiled core. See e.g., U.S. patent application Ser. No. 12/925,765 for profiled core designs, which document is incorporated by reference and made a part of the disclosure. The profiled core structure provides improved diaper performance by providing more absorbent material in areas of the core where it is needed. The profile may also be achieved by stacking multiple layers of the absorbent composite, but at different lengths (e.g., short top core, full length bottom core). A more efficient solution may be to vary the SAP dosing rate during application of the SAP and align the high SAP dose areas with the crotch area of the diaper when the core is converted in the diaper line. Such a method may be more efficient as it utilizes less nonwoven material than the stacked core. It is also cost effective.

In one embodiment, a powdered hotmelt adhesive is mixed with the SAP to provide additional bonding. The SAP and adhesive mixture is distributed between the two nonwoven webs and the hotmelt adhesive is "activated" by passing the composite through a heating device. Suitable devices include heated rollers, infra-red heater and the like. The adhesive melts and bonds the SAP and nonwovens together. This can also be combined with the patterned embossing/ultrasonic processes to produce pocket patterns as described previously. Typically, the adhesive/SAP is mixed at a ratio of 10 to 100 parts SAP to 1 part adhesive by weight (1-10% adhesive by weight). Too much adhesive will limit the absorption performance of the SAP, while too little adhesive may sacrifice structural integrity. Preferably, the adhesive is applied at a rate of about 1 to 2 particles of adhesive per particle of SAP. The exact rates may be worked out if the average particle size and density of the SAP and adhesive are known.

The absorbent composites described thus far are well suited for manufacturing in both offline and online manufacturing processes. In the offline process, the core machine stands separate to any other process and produces rolls, spools or boxes of festooned material that is then delivered to the diaper converting line. Typically, but not necessarily, the machine associated with the product of FIGS. 6-7, as described previously, would produce a wide sheet of the absorbent composite. The product is then slit to produce a number of rolls of material for use on the diaper converting line, e.g., a 1.5 m wide machine would produce 15 rolls of material at 100 mm width. In the offline process, the offline machine will typically run at speeds much slower than the diaper converting line. In the online process, the core machine is part of the diaper converting line and the core is made a part of the diaper converting process. The output speed of the core machine must match the speed of the diaper converting line and the width of the core will match the width of the core in the product.

In an offline process depicted in FIG. 18A, a SAP sandwich is formed having a substrate A, a second substrate B, and a SAP coating disposed between the two substrates. In one embodiment, the SAP is immobilized by bonding the two substrates together to contain the SAP in discrete planar volumes between the layers. One or a combination of the following methods for SAP stabilization may be employed. In a first process, heat embossing or ultrasonic bonding is employed to fuse the substrate layers in a defined pattern. In a second process, an adhesive is applied to one or both of the substrate inner surfaces. The two substrates are then strategically bonded together according to an advantageous embossing pattern. Thirdly, a thermal binder, such as low melting adhesive particles, may be mixed with the SAP particles. External heating is then applied to the composite to activate or melt the adhesive, thereby binding the particles to the substrate and to each other. Here, a patterned embossing step may be used to enhance the lamination quality while maintaining a more open SAP layer structure for enhanced liquid intake. If a patterned is not desired, a smooth calendar roll (not patterned) may also be employed to bond the cover layer to the SAP layer to produce the sandwich structure.

In an online process, the core forming process is directly coupled to the diaper converting process. The SAP sandwich structure is formed as with the first and second process discussed above, at speeds 3-4 times that of the offline process. The third method may not be suited to the faster online process because of the short dwell time required to heat and activate the thermal binder that is mixed in with the SAP. The offline process is designed to produce a wide material at slower speeds. The material output is then slit into narrower widths to supply several diaper lines. In contrast, the online process is designed to produce a narrow (1-wide) material at higher speeds and supply core material for only one diaper machine at a time.

So, in a preferred embodiment using the offline method according to the third method described above, a small quantity (10% or less) of hot melt particles is mixed in with the SAP. This particle mix is uniformly deposited on substrate A and then, subjected to radiant IR heating to melt the adhesive particles. The second substrate B is then laid on top while the material is still hot. The layers are immediately laminated together using heat embossing with a patterned roll/smooth anvil embossing system. Table 2 below summarizes the process and provides certain parameters of a preferred embodiment.

TABLE 2

Exemplary Offline Process of Manufacturing Using Hot Melt Adhesive

| Core Structure | Substrate A | SAP BW, gsm | Hot Melt | Activation | Substrate B | Bonding Pattern |
|---|---|---|---|---|---|---|
| A | 20-80 gsm ADL web | 150-750 | Abifor 1605, 5-10% | IR Heating | Tissue | Diamond, 22 × 50 mm |

Figure 18C:
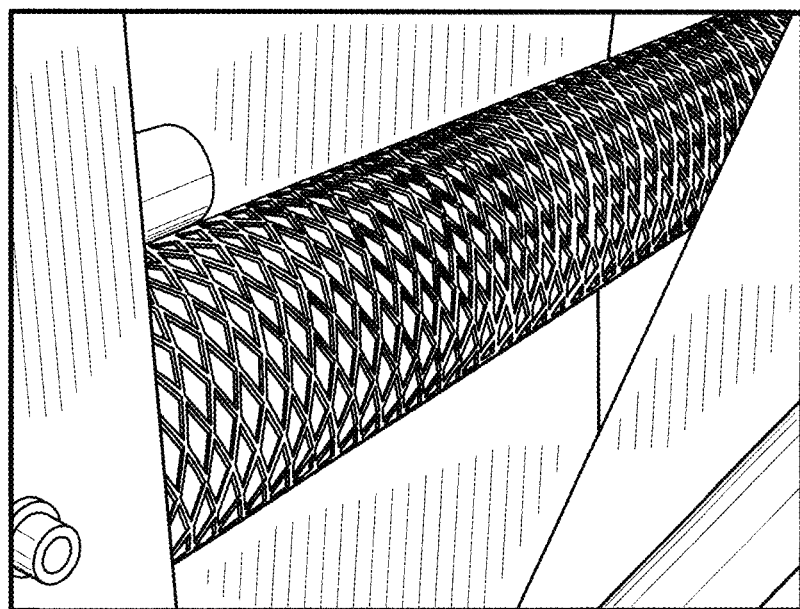

A coating line manufactured by Santex, Tobel, in Switzerland may provide the SAP scattering technology, IR heating and web handling. See e.g., FIG. 18B. As shown in FIG. 18B, a scatter unit utilizes a hopper and a standard rotating needle roll to mix and apply the mixture on the web. The SAP material is chosen according to its suitability for the application, but in general, SAP with high retention capacity and high absorbency under load are preferred, for example, Centrifuge Retention Capacity (CRC) of from 20-40 g/g, a Pressure Absorbency Index (PAI) greater than 100 g/g An exemplary SAP is M-151 manufactured by Nippon Shokubai. A suitable hot melt adhesive is low melting EVA polymer, Abifor 1605, 0-200 micron particle size grade, which is currently available from Abifor Powder Technology, Switzerland. As shown in the detail of FIG. 18, a readily available scatter unit employs a needle roll in mixing and applying the mixture on the web. The bonding pattern specified for this embodiment is an elongated diamond with a major axis length of 50 mm oriented in the MD direction and a minor axis length of 22 mm. See e.g., FIG. 18C.

Figure 19:
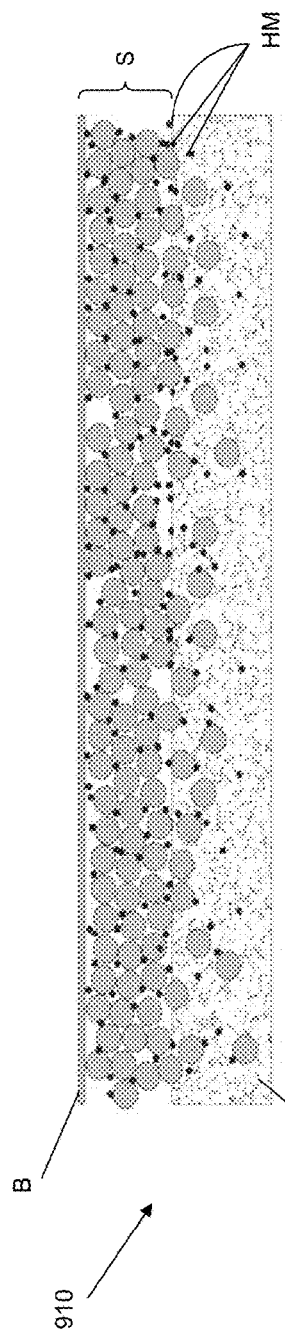
FIG. 19 is a simplified cross-sectional view representing an absorbent composite in accordance with the process of FIG. 18A.

FIG. 19 depicts an absorbent composite 910 that is produced by the method and system as described in respect to FIGS. 18A-18C above. Preferably, the composite 910 includes a bottom substrate A that is a bulky nonwoven, a top layer or substrate B, and superabsorbent particles S situated between the two layers and interspersed with hot melt adhesive particles HM (as described above). More preferably, the top substrate B is provided by a tissue material readily available and understood in the art. The top substrate B may, in the alternative, be provided by a second bulky nonwoven layer or an SMS or spunbond ("non-bulky") nonwoven layer.

As described above, a laminate of the absorbent composite 910 may be manufactured on-line or off-line. The laminate may be modified to incorporate additional or differential SAP loading (i.e., Profiled Core) as also discussed above. In an off-line process, the composite may be delivered as a wide sheet that is slitted and divided into individual core composite sections.

Figure 20A:
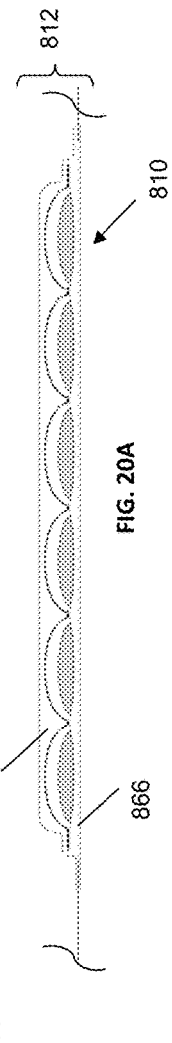
FIG. 20A is a simplified cross-sectional view across a lateral centerline of a disposable absorbent article employing an absorbent core laminate in accordance with a preferred embodiment of the disclosure.
Figure 20B:
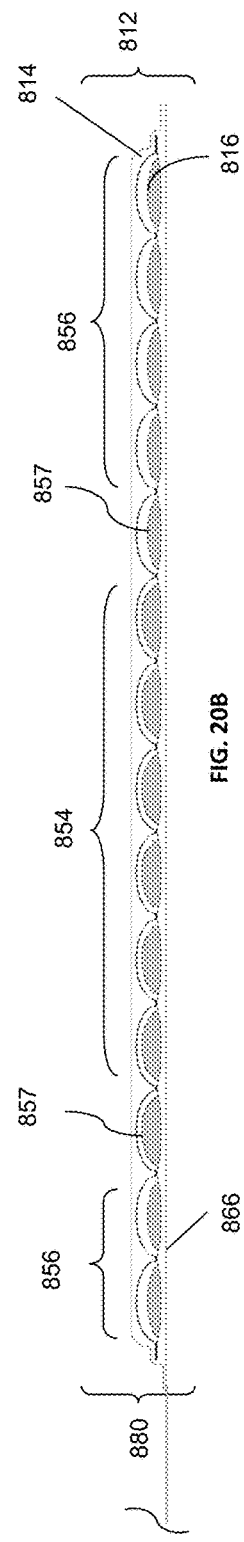
FIG. 20B is a simplified cross-sectional view across a longitudinal centerline of a disposable absorbent article employing an absorbent core laminate in accordance with a preferred embodiment of the disclosure.
Figure 20C:
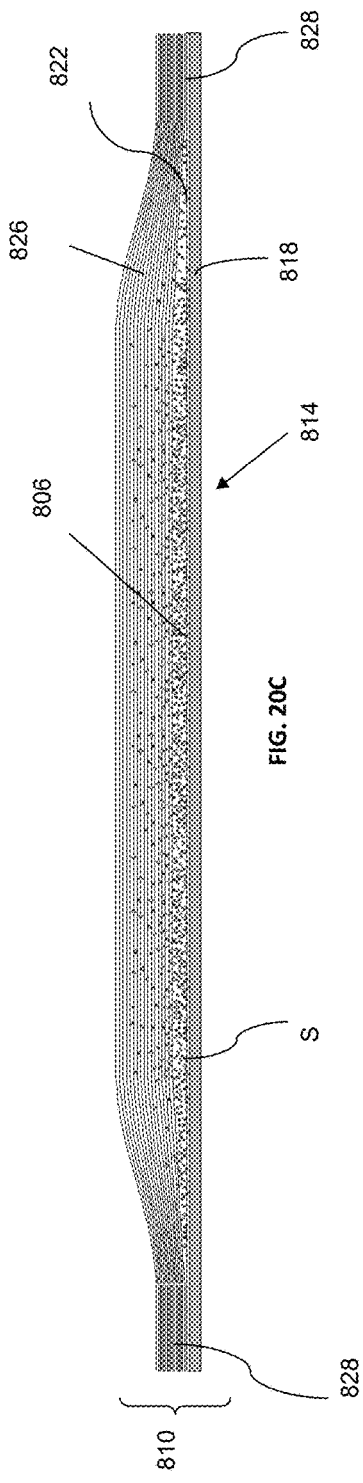
FIG. 20C is a simplified cross-sectional view of an absorbent composite in the absorbent core laminate of FIGS. 20A and 20B.

FIGS. 20A and 20B are cross-sectional views of a disposable absorbent article 812 (laid flat) incorporating an absorbent core laminate 812 or absorbent composite 810. For convenience in describing the accompanying Figures, a complete absorbent composite extended to provide a complete absorbent core of a disposable absorbent article may be referred to as an absorbent core laminate while an absorbent composite may be used to describe components of a section or portion of the laminate. Elsewhere, including the claims, the terms may be used interchangeably. The absorbent core laminate 812 features a plurality of spaced apart pockets 814 with an aggregate 816 of SAP (superabsorbent particles (S)) contained therein. FIG. 20C provides a detail cross-sectional, elevated view of one of these pockets 814. FIG. 20C also depicts the components of a preferred absorbent composite 810.

Now referring to FIG. 28, a basic disposable absorbent article 862 (in a laid flat state) is shown incorporating an absorbent core laminate 812 as the absorbent core, according to the disclosure. The absorbent core laminate 860 is completely covered by a topsheet 864 but, for convenience, the topsheet 864 is shown to be transparent. The absorbent core laminate 860 is supported on a wide backsheet 866 with side margins 868. Each side margins 868 is provided with a cutout that exhibit a concave shape on either side of the absorbent core laminate 860. As generally known, the concave cutout will coincide or correspond to leg holes about the thighs of the user.

Referring again to FIG. 20C, in a preferred construction, a nonwoven material provides a base or bottom layer 818 of the composite (during manufacture of the absorbent article product). During product use, the base layer 818 may be described as being positioned away from the body, as opposed to being positioned on the body-side of the absorbent composite 810 in direct receipt of intake. Further in this embodiment, the base nonwoven layer 818 has an adhesive layer 822 applied thereon. The adhesive layer 822 is preferably delivered, as a continuous bead, atop the base nonwoven 818 and in an advantageous open pattern, as will be described below.

The absorbent composite also includes a SAP layer 806 positioned above the adhesive layer 822 and in between the bottom nonwoven 818 and a top nonwoven layer 826. In this embodiment, the SAP layer 824 is composed of SAP particles S only, without any form of binder material or matrix. It may be described also as being fluffless or pulpless. The top nonwoven layer 826 is preferably provided by a bulky nonwoven material with fibers that extend toward and laterally entangle some SAP on or near the top surface of the SAP layer 806. The top nonwoven 826 is preferably bonded to the base nonwoven 818 by embossing and more preferably, by point bonding. Bond points 828 define the periphery of the pocket 814 and also, compress the resilient bulky nonwoven 826 at the pocket periphery to present an overall bubble or domed cross section (as shown in FIG. 20C). The simplified illustration of FIG. 29 provides an alternate view of the absorbent composite 810 and, more particularly, the components of the composite, without showing point bonding and compression about the periphery of the pocket 814.

In this preferred construction, the bulky non-woven layer 826 contacts and covers the SAP layer 824 thereby restricting travel of SAP particles S. The bulky non-woven layer 826 is also advantageously positioned as a top layer during manufacturing and product handling, thereby restricting travel or migration of SAP particles even before use. During use of the absorbent article, the bulky non-woven 826 is also advantageously positioned on the bodyside to receive and distribute intake to the SAP layer and beyond.

In this preferred construction, the SAP is organized into discrete, spaced-apart aggregates or clumps 816 of SAP, each of which is maintained in a pocket or container 814 as described previously. The two non-woven layers 818, 826 are bonded at bond sites or, more specifically, at an arrangement of discrete, spaced-apart bond points 828. The bulky non-woven 826 is, therefore, multiply and intermittently secured over the SAP aggregates 816, and helps maintain the SAP aggregates 816 in place. The unique functions and properties imparted on the absorbent composite and absorbent core laminate through use of the bulky nonwoven are described further below.

The exploded view of FIG. 21 reveals the various components or layers of the absorbent composite 810 or absorbent laminate 812 and their relative positions, according to a preferred embodiment. FIG. 22 provides additional exploded views that illustrate a basic process or steps for making the composite, by showing the order by which the components of the composite are brought together. Reference should also be made to preceding descriptions of making an absorbent composite or an absorbent article employing the composite, including FIGS. 1-5 and descriptions associated therewith. Many of the process steps and process components described therein may be applicable or adaptable for use in the making of the absorbent composite of FIGS. 19-29.

In an initial step of the preferred method, a web of nonwoven 818 is conveyed in the conventional manner and then, passed beside an adhesive applicator. The spray adhesive applicator preferably delivers a continuous bead onto the nonwoven 818 in an open adhesive pattern (see FIG. 22A). In this way, loops of adhesive 822*a* are provided on the surface of the nonwoven material 818 characterized by or defining open regions free of adhesive (rather than a uniform layer or film). The loops 822*a* in exemplary embodiments are smaller (i.e., width or diameter) than the pockets 814 previously described, with diameters typically in the order of 1 mm to 25 mm.

FIG. 22B illustrates the delivery of SAP aggregates 816 by methods described herein, or otherwise known in the art, onto a substrate composed of the base nonwoven layer 818 with an adhesive layer 822 or open pattern pre-applied thereon. Specifically, SAP is delivered via an airstream and, through the use of a conventional vacuum system or suction mechanism, such as those previously described herein or otherwise known in the art. Suction applied on and beneath the web of nonwoven 818 draws SAP toward the nonwoven 818 and organizes the SAP into the desired prearrangement of aggregates or clumps 816 of SAP (as shown in FIG. 22B). The vacuum system may employ a screen or mesh interface to better engage the bottom of the non-woven and define the target geometry of the SAP aggregates. Thus, the interface presents a suction pattern that corresponds with the desired pocket pattern of the SAP aggregates 816. The vacuum system preferably draws the SAP directly from the stream above the web and into discrete clumps or aggregates on the web above the suction mechanism. Certain regions, including regions along the sides and ends are designated as SAP-free (as well as adhesive-free) zones and will be purposely left free of SAP.

SAP generally falls directly into the desired arrangement as opposed to being first distributed across the web and then moved about the web before forming tighter concentrations on the web (as in alternate embodiments). The SAP generally does not have to travel over adhesive on the web to form the target plurality of SAP aggregates 816. The resulting web is, therefore, composed of a nonwoven base layer 818 with an open adhesive pattern 822 thereon and an arrangement or layer 806 of discrete, spaced apart SAP aggregates 816. The clumps of SAP generally lay on and contact the adhesive, but the open pattern of the adhesive occupies substantially less than the bottom layer of that SAP aggregate contacts. It should be noted, however, that a SAP particle contacting adhesive may be generally immobilized. Another SAP particle positioned adjacent and in contact with such immobilized SAP particle may, in turn, be restricted (in movement) by and at least partly immobilized by that SAP particle (and/or other adjacent SAP particles). Such friction mechanism at least hinders horizontal movement of SAP particles.

As the web of nonwoven-SAP moves forward and away from the vacuum system, the adhesive pattern 822 acts to maintain the desired arrangement and position of SAP aggregates 816. In a subsequent step, a web of a second nonwoven 826 is conveyed toward and then applied over the nonwoven-SAP laminate. See FIG. 22C. As discussed above, the preferred top nonwoven 826 layer is a bulky nonwoven. With further processing and travel of the SAP aggregates 816 in a process of making an absorbent article such as a diaper or training pants, the additional nonwoven 826 provides additional cover and acts to retain the SAP aggregates 816 in the desired pattern. In addition to providing advantageous functions in the finished product and during use, the bulky nonwoven 826 entangles top layered SAP particles S, as represented in FIG. 29, thereby furthering the immobilization of the SAP aggregates 816 (during product manufacture and then post-manufacture product handling). Entanglement of the SAP with the fibers of the bulky nonwoven restricts lateral and vertical movement of SAP near the top of the SAP aggregate 816 and also hinders movement of SAP directly beneath it. As noted herein, the SAP and bulky nonwoven are defined and selected in consideration of the desired degree of entanglement and penetration.

Next, the web of two nonwovens and SAP aggregates therebetween is passed over to a calendar roll that engages and compresses the web. The calendar roll is equipped with a surface engraving having a pattern that corresponds with the pocket pattern on the web, as described previously. FIG. 23 depicts a typical bonded absorbent composite laminate 812 using discontinuous point bonding. The dots reflect indentation in the bulky nonwoven 826 after embossing. The dots are also the bond points 828 for the pockets 814 (see also the cross-sectional views of FIGS. 20A-20C). Securing the two nonwovens together about the SAP aggregates 816 provides another mechanism for maintaining the arrangement of SAP aggregates 816 and the resultant absorbent laminate 812. As will be discussed herein, the arrangement of bond sites provides a geometric grid 830 that locate and define the pockets 814 of SAP aggregates 816.

Thus, in this exemplary embodiment, the preferred SAP laminate construction draws from several structural features to inhibit the migration of SAP particles from the desired arrangement of SAP aggregates during absorbent article product manufacture and post-manufacture handling. First, adhesive is provided on the base non-woven layer and SAP aggregates are laid on the adhesive. The optional adhesive layer is delivered, however, in an open pattern of closed loops that contact only certain bottom layered SAP particles but inhibit travel of SAP particles beyond these contacted SAP articles. The application of the top nonwoven layer over the SAP aggregates augments the minimally-applied adhesive to further restrict movement of the SAP. Advantageously, the SAP layer delivered onto the base nonwoven is pulp-free and free of a matrix or binder, which optimizes the composite's absorption and fluid handling properties. It is also free of adhesive but for the bottom layer of adhesive. Thus, much of the SAP layer, particularly, the middle part of the SAP layer, consists of SAP, although other materials may, in alternative embodiments, be included to impart beneficial properties. The predominance of the SAP-only constituency results in a thinner, softer, more flexible SAP construction, as discussed previously. Also, the large sections of SAP-only constitution, which are adequately maintained in position (inhibiting SAP particle migration), provide improved absorbent properties and fluid handling characteristics.

As a further enhancement, the preferred SAP laminate construction utilizes an arrangement of discrete or intermittent bonding points in conjunction with the laminate construction of FIG. 22. See FIG. 23. The embossing pattern that provides the intermittent or spaced part bonding points provides a synergistic effect with utilization of the SAP laminate construction of FIGS. 20-22 and/or the use of a bulky nonwoven layer as a top or bodyside layer of the absorbent laminate (or vice versa). The gap provided between bond points allow for fluid to pass between SAP aggregates, including fluid flow passing from the SAP-only middle sections of the SAP laminate. The provision of the bulky nonwoven and/or adhesive reduces the need for complete or continuous bonding lines. Similarly, the position of the bulky nonwoven and/or point bonding reduces the amount of adhesive required for SAP stabilization.

Furthermore, reduced constriction of the bulky nonwoven layer by using the embossing points, rather than longer bond points or solid bond lines, allow for the resilient bulky woven to expand and advantageously receive and distribute fluid intake. Pressure applied by the embossing compresses the bulky nonwoven at the bond point as shown in FIG. 20C, but the resilient bulky nonwoven "bounces up" from the bond point. See also FIG. 30. This results in a more open substructure well capable of fluid handling functions. Further, the SAP-only constituent functions to receive and absorb the fluid intake and, as necessary, pass fluid intake to adjacent SAP pockets via the gap between bonds. In one respect, there is a fluid channel that runs from the top surface of the relatively open bulky nonwoven layer, through the bulky nonwoven layer, and into the SAP-only body, and from the SAP-only body middle layer, sideways through the gap between bond points, and then into another preferably, substantially SAP-only aggregate.

The plan view of FIG. 24 presents a bonded absorbent core laminate 812 mutually secured by discrete bond points 828. FIG. 24 depicts a preferred pattern of SAP pockets 814, according to this exemplary embodiment. The laminate 812 is elongated having a lateral width dimension and a longitudinal length dimension. The shape of the laminate 812 at this stage is generally rectangular. The embossing process preferably employs an intermittent bonding pattern to enhance fluid flow between pockets, as described above. The selected pocket pattern uses diamond shaped embossing to produce diamond shaped pockets 814. An advantage to the use of a diamond shape pockets and the corresponding grid is that, with its straight, intersecting lines, it is easier to design and match engraving patterns on embossing rolls and interfaces for vacuum systems.

Preferably, the diamond shapes are arranged such that the embossing lines or series of bond points are not square with the side margins of the core. The straight lines (SL) that aligned bond sites may present on the surface of the laminate 812 are advantageously oriented at less than a ninety degree angle to the side margins and more preferably, between about 60 degrees and 30 degrees. In this way, the interconnected bonding lines (SL), which can provide a potential fluid pathway (i.e., above the surface as well as in the pockets 814 and along the lines) are longer than a perpendicular line to the side margins 834 (which another pattern may represent). This addresses possible fluid leakage to the side margin 834 and encourages fluid path diversion into non-saturated pockets downstream.

The absorbent core laminate 812 also features SAP free lanes 838 proximate side margins 834 and proximate end margins 836. The steps for delivering SAP and organizing SAP aggregates on the bottom nonwoven layer are designed to leave these regions free of SAP to minimized SAP usage. The regions are later sealed and in the case of the side margins, a curved section may be cut out of the absorbent core laminate 812 to accommodate leg cutouts and/or produce an hourglass shaped core. The absence of SAP in these regions makes for a more flexible and foldable material layers. This also avoids having to cut (or seal) through the relatively harder, stiffer SAP material as may be required in the manufacturing process, thereby promoting cleaner and more precise cuts (and seals). Perhaps, more importantly, this avoids extra wear on cutting blades and maintenance and downtime of manufacturing equipment.

The plan view of FIG. 25 illustrates an alternative absorbent core laminate 840 employing an alternative pocket pattern and bonding pattern. Instead of intermittent bonding, the bond pattern employs continuous bond lines 842 that generates a solid grid. As with the previously described embodiment, diamond shaped pockets 844 are used. Among other things, the potential fluid pathway created by the connection of the bond lines is directed to an angle away from the side margin (i.e., 45 degrees), thereby somewhat mitigating the risk of direct fluid strand to side margin.

As used herein, diamond shaped pockets mean a pocket having four sides and with two corners preferably mutually aligned with the longitudinal direction and the other two corners with the lateral directions. The pockets are preferably not oriented as rectangles square with the lateral and longitudinal centerlines of the laminate, wherein bond lines make for a "direct" straight line path to the side margins. As used herein, the term "grid" means the geometry established by intersecting lines along the bond sites or embossing line. Further, as used herein in respect to an arrangement or geometry of pockets, "direct" straight line path means one or more bond lines that connect to make for a continuous and unobstructed (not "broken") path from proximate the longitudinal centerline to the side margins wherein, the path is generally perpendicular to the side margins. Such a direct straight line path makes for the shortest fluid path to the side margins. For clarity, such straight line paths that are more than thirty degrees deviated from the perpendicular shall be referred to as an indirect straight line path and do not direct straight line paths. Straight line paths that are not so deviated are considered "direct straight" line paths.

It should be noted that other "grids" and other pockets shapes and pocket arrangements may be employed. Some pocket shapes employed will not exhibit any direct or for that matter, any straight line, paths to the side margins. These include some arrangements previously described herein, including arrangement of circle or elliptical shaped pockets.

Profiled Core Composite

In this preferred embodiment, the method of manufacturing an absorbent core includes steps for delivering a profiled core construction. The method is a further version of the method previously described, and in one preferred process, incorporates all of the steps of the previous method. For example, while the earlier method may employ a single SAP applicator, the present method employs a second SAP applicator to augment SAP delivery by the first SAP applicator. The second SAP applicator may be positioned upstream (in front) or downstream of the first applicator. Whereas a nozzle of the first applicator may be sized to cover the width of the target core, the second applicator may be sized to cover a narrowed portion of the core. Further, the second applicator may be programmed for delivery for a specified period that is a fraction of the delivery period of the first applicator. For example, the first applicator may be programmed to continuously deliver to almost the entire width of the SAP core (except for a narrow SAP-free lane at the side margins). The second applicator may be sized and programmed to deliver SAP to a narrower central region and/or for an intermittent period that will correspond to a central region of the core. In exemplary embodiments, the second SAP applicator is positioned downstream of the first SAP applicator thereby delivering a second dose or load of SAP over the SAP first deposited on the web of nonwoven. Thus, the arrangements of SAP aggregates sourced by the second applicator (as well as the first applicator) have a higher SAP loading than other SAP aggregates sourced only by the first applicator.

As before, the preferred process employs suction mechanisms and screens to organize the SAP pockets on the web. Upon delivery, the SAP loads are quickly drawn into the SAP aggregate formation. SAP aggregates sourced by two SAP applicators provide pockets with a thicker and larger SAP layer, than pockets that are not so sourced.

In the preferred arrangement, the dual SAP-loaded pockets are located in a central region where most intake occurs. In further embodiments, the constituents of the two SAP loadings may be varied to achieve a desired mixture or the desired absorbent or fluid handling properties. In yet further embodiments, additional SAP applicators may be employed and strategically located to produce the desired SAP pocket pattern and function.

Use of Bulky Nonwovens

The "bulky" nonwoven referred to herein is, and provides, an open, fibrous network or web of hydrophilic but non-absorbent fibres. Further, as used herein, a bulky nonwovens is a fibrous web material having a thickness of between 100 µm and 10,000 µm (preferably 1,000 µm to 5,000 µm), basis weight between 15 g/m$^2$ and 200 g/m$^2$ (preferably, between 20 g/m$^2$ and 80 g/m$^2$), and density between 0.01 g/cc and 0.3 g/cc (preferably between 0.01-0.08 g/cc). Moreover, the bulky nonwoven will have an effective pore diameter between 300 µm to 2000 µm. Typically, particles of the SAP selected will have an average particle size of about 300 µm, which ensures some penetration or entanglement between SAP and the selected bulky nonwoven. The tables shown in FIGS. 31 and 32 may be used in further defining the bulky nonwoven and showing the interrelation between the key properties. (The shaded areas in the Tables of FIGS. 31 and 32 point to bulky nonwoven materials according to the disclosure.) The effective pore diameter is estimated from web density, fiber diameter and fiber density values following the method of Dunstan & White, J. Colloid Interface Sci, 111 (1986), 60 wherein effective pore diameter=4*(1−solid volume fraction)/(solid volume fraction*solid density*solid specific surface area).

Suitable fibres include polypropylene (PP), polyethylene (PE), polyethylene terephthalate (PET), polylactic acid (PLA), polyolefins, copolymers thereof and any combination thereof including bicomponent fibres. The fibres are usually treated with a surface active agent, surfactant, to modify the surface tension of the fibres so that they are hydrophilic.

As described above in respect to FIGS. 16 and 17, there are fluid handling benefits that arise from the employment of a bulky nonwoven as a fabric in the absorbent composite. Furthermore, orientation of the absorbent composite with the bulky nonwoven positioned on the body side is particularly advantageous as it enhances the absorbent composite's capacity for acquisition and distribution of fluid intake. The bulky nonwoven has a high void volume and permeability, and allows the composite to quickly capture and efficiently distribute the fluid away from the insult point.

Additionally, the bulky nonwoven with the embossing patterns described also has the following features:

The "pillow" structure (see e.g., FIG. 20C, FIG. 29 and FIG. 30) provided by the bulky nonwoven as a bodyside layer creates a compressible and resilient structure that enhances the perception of softness.

Figure 30:
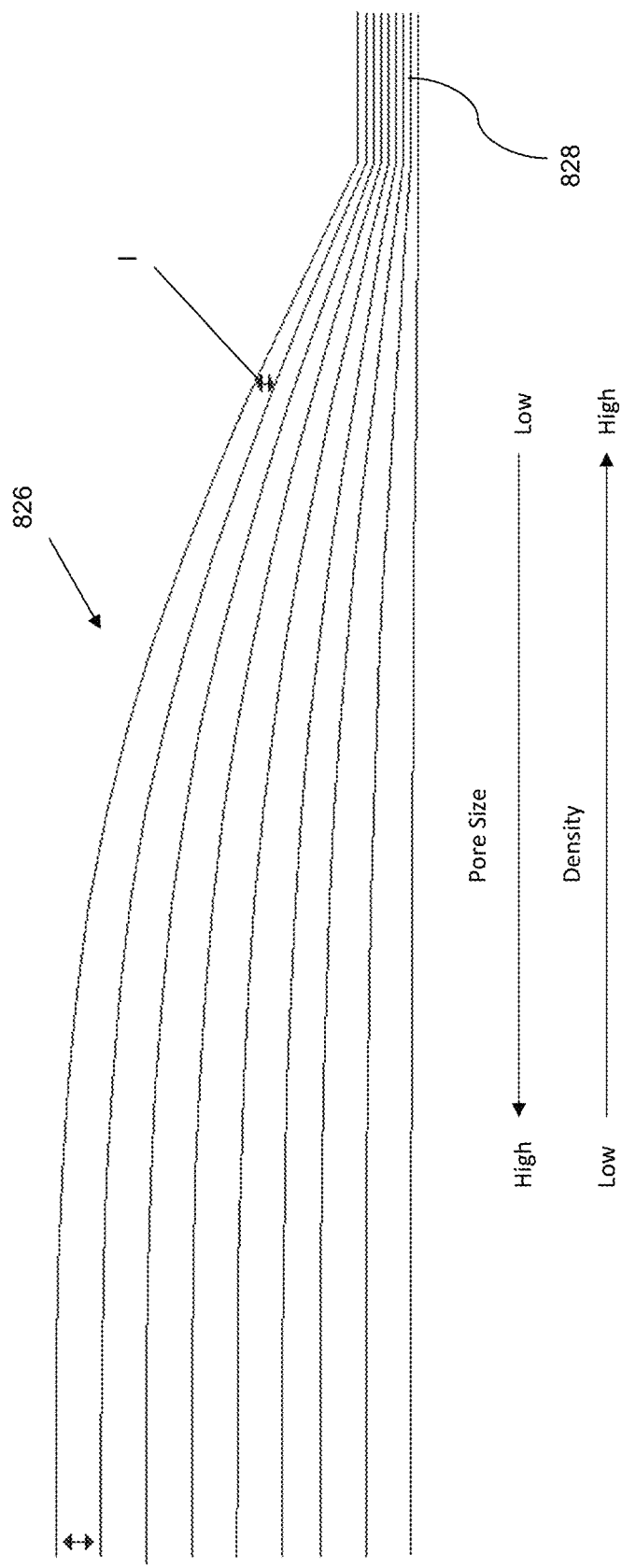
FIG. 30 is a simplified illustration in partial cross sectional view of a bulky nonwoven layer point bonded in an absorbent composite according to the disclosure.

Within a pocket area, a pore size gradient exists (see e.g., FIG. 20C and FIG. 30) that encourages the liquid to move from the crests (more open area with larger interfiber distance, I) to the bonded area (more dense area with smaller interfiber spacing). This is illustrated in FIG. 30 which shows the bulky nonwoven 826 exhibiting smaller interfiber distances I toward the bond point 828. Since capillarity is inversely related to density, the capillarity of the denser area is higher than the more open area hence liquid within the nonwoven will tend to be drawn towards the denser areas. This is particularly important for dryness perception since it allows any remaining liquid at the crests to drain away towards the bonded areas and further into the underlying SAP structure where the liquid is tightly held. Hence, a top surface that is relatively free of liquid is created which contributes to the perception of dryness. This pore gradient also discourages fluid from flowing back to the surface.

The discontinuous bonding pattern also contributes to the softness perception by creating a more flexible composite.

Spray Adhesive

Adhesives can be used to provide additional bonding for the composite and can be used to help secure the SAP on the nonwoven. This is needed during manufacture of the composite, subsequent and further processing of the disposable absorbent article incorporating the composite, and the storage and eventual use of the composite in the absorbent article. Ideally, the adhesive is applied to at least one of the nonwoven webs of the composite or adhesive can be applied to both the upper and lower nonwoven webs.

Suitable adhesives include hotmelt adhesives that are applied by either a slot coat or a spray coat applicator (such as those supplied by Nordson Corporation). In a preferred embodiment, the adhesive is applied by a spray method where continuous beads of hotmelt adhesive are directed by air streams into patterns, such as a spiral pattern or a more random pattern. FIG. 22 show one such pattern. The diameter of the spiral is in the range of 1 mm to 25 mm. The advantage of such spray patterns is that the adhesive coverage on the nonwoven web is not uniform and there are open areas that are substantially free of adhesive. These open areas provide unrestricted access for fluid flow through the nonwoven web and into the superabsorbent layer, whereas a uniform coating may slow down or reduce the flow of fluid through the web.

To illustrate possible variations of the preferred embodiment, FIG. 26 provides an exploded view of an absorbent core laminate 850 according to an alternate embodiment. The absorbent core laminate 850 employs a base nonwoven layer 818 with an adhesive pattern 822 pre-applied thereon, as described previously. The laminate 850 also provides a first layer 816 of spaced apart SAP aggregates that occupy substantially all of the lateral and longitudinal expanse of the laminate 850. The adhesive pattern 822 and the SAP aggregates may be applied as described previously, with the SAP being delivered by a SAP applicator and organized into the desired pocket pattern with the aid of a conventional vacuum system and the like, as described previously. In this variation, a second SAP applicator may be positioned downstream of the first SAP applicator to deposit SAP onto a selected region(s) of the web having the first layer 816 of SAP aggregates already provided thereon. A region selected to receive additional SAP constituent or perhaps, absorbent material having properties different from the SAP first delivered, is typically a central region that will correspond to a crotch region when the disposable absorbent article is in use. In the process in which the machine direction of the laminate 850 coincides with the lateral direction, the SAP applicator may be equipped with a nozzle or spray area that is narrower than that of the first SAP applicator. The region on which SAP is delivered will, therefore, be narrower than the SAP layer 816. If the machine direction coincides with the longitudinal direction, the second SAP applicator may be programmed to deliver SAP only during a period aligned with travel of the central region under the second SAP applicator.

Referring to FIGS. 20A and 20B, the pockets 814 in a central region 854 contain concentrations or SAP aggregates that are greater than SAP concentrations in pockets 814 near longitudinal end regions 856 of the absorbent core laminate 812. Intermediate of these regions and the central regions, there are pockets 857 containing SAP in concentrations that is somewhere in the middle. The concentrations of SAP in these pockets 857 may be determined by the extent of the second SAP applicator and possibly a sharing of excess SAP between adjacent pockets. These pockets 857 may serve as a gradual transition between high and low capacities of SAP and absorption and swell properties, and may produce beneficial fluid flow (across the absorbent core), as discussed herein.

Referring again to FIG. 26, this embodiment is also equipped with a second adhesive pattern 862 to help secure SAP in the pockets. The adhesive pattern 862 may be identical to the open pattern 822 preferred for application on the bottom nonwoven, and will be pre-applied to the top nonwoven 826 before introduction of the top nonwoven 826 into the resulting laminate 850. In the resulting construction, this second adhesive pattern 862 helps secure particles of the SAP aggregate that contact or nearly contact the top nonwoven 826. If a bulky nonwoven is employed as a top nonwoven 826, the adhesive helps secure SAP in the top layer region of the SAP aggregate with fibers of the bulky nonwoven, including promoting SAP entanglement. It is possible that when two adhesive patterns are employed in a laminate design, as with the laminate of FIG. 26, the total amount of adhesive (e.g., thickness of the bead, size of the loops) used in each pattern may be reduced. Moreover, the number or frequency of bond points may also be reduced. The various mechanisms for securing SAP in the pockets 814 act differently on the SAP and from various perspectives, but work together to obtain a common objective.

FIG. 27 illustrates a subsequent stage in an exemplary process of making an absorbent core laminate and/or disposable absorbent article. A web 870 of separable absorbent core laminates 872 is shown being conveyed with the lateral direction coinciding with the machine direction. The laminates 872 are shown being prepared with an hourglass shape. The delivery of SAP onto the bottom nonwoven is provided such that SAP-free regions 874 are present near or along the eventual side margins 876 of individual absorbent core laminates. Furthermore, as shown in FIG. 27, wider regions 878 near the center of the side margins 876 are also void of SAP in preparation of a cut to accommodate a leg hole and/or simply, produce the preferably hourglass shape that helps to more readily fit or accommodate the user around the crotch region. In this way, SAP usage and material cost may be reduced.

In any event, a narrow region or layer 852 of SAP aggregates is deposited atop the first layer 816, and in the selected central region. The vacuum system may again be employed to direct the deposit of SAP to the target areas. In this way, SAP aggregates of higher concentrations are generated.

Typically, the absorbent core laminate 812 is elongated with a pair of longitudinally-spaced apart end regions 856 and a central region 854 therebetween. The absorbent core laminate is situated between the topsheet and backsheet in what is referred to as a "core envelope" 880. See also cross-sections FIGS. 20A and 20B. FIG. 20A may be described as a cross-sectional view laterally across the core envelope 880 (i.e., a cross lateral centerline XX) while FIG. 20B is a cross-sectional view longitudinally across the core envelope 880 (i.e., across longitudinal centerline YY). Absorbent core laminate 812 may also be described as having side margins that extend between the end regions 856. An arrangement of the pockets 814 of SAP aggregates 816 is set between the side margins 812. As can be seen from the drawings, the arrangement defines a pattern or grid on the absorbent core laminate 812. About the central region 854, a pair of cutouts 882 into the side margin 856 provides a concavity in the generally rectangular laminate 812, which reduces the population of pockets 814 in the central region 854. The concavity makes for a generally hourglass shape to the absorbent core laminate 812. As the central region 854 generally corresponds with crotch region of the disposable absorbent article 862, the concavity of the absorbent laminate 812 and general absence of the relatively stiffer (than the topsheet and backsheet material) core material facilitates the deformation of the absorbent article 862 in the crotch region during use and helps to accommodate the contour of the user.

The present disclosure is, therefore, well adapted to carry out the objects and attain the ends and the advantages mentioned, as well as others inherent therein. While presently preferred embodiments (in the form of a diaper) have been described, numerous changes to the details of construction, arrangement of the article's parts or components, and the steps to the processes may be made. For example, the various topsheets, backsheet, absorbent core, containment walls and other absorbent composite structures may be utilized in other parts of the article or with other articles other than diapers. Such changes will readily suggest themselves of those skilled in the art and are encompassed within the spirit of invention and in the scope of the appended claims.

Although the present disclosure and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of making a disposable absorbent article, said method comprising:
conveying a first fabric into position to receive superabsorbent particles (SAP);
depositing superabsorbent particles on said first fabric to provide discrete aggregates of SAP free of an absorbent matrix;
conveying a second fabric such that the second fabric is moved toward the first fabric, and wherein the first fabric or the second fabric is bulky nonwoven, wherein the bulky nonwoven is a pulpless, open, fibrous network of non-absorbent and hydrophilic fibers;
positioning the second fabric relative to said first fabric such that fibers of said bulky nonwoven entangle particles of said aggregates of SAP, thereby securing, at least partly, the aggregates of SAP; and
bonding said first and second fabric at a network of bond sites to form a pulpless elongated absorbent core laminate having a plurality of pockets of aggregates of SAP, whereby each pocket is positioned about an aggregate of SAP;
conveying the elongated absorbent core laminate, whereby said bulky nonwoven and said pockets inhibit SAP migration from said pockets;
situating the elongated absorbent core laminate between a topsheet and a backsheet, thereby forming a core envelope of said topsheet, backsheet, and elongated absorbent core laminate, the topsheet and backsheet further providing a chassis supporting said elongated absorbent core laminate;
forming leg holes in said chassis; and
joining end regions of said chassis to form a disposable absorbent article, whereby said bulky nonwoven and said pockets inhibit SAP migration from said pockets.

2. The method of claim 1, wherein said conveying said first fabric is preceded by applying an adhesive pattern on said first fabric.

3. The method of claim 2, wherein said applying adhesive includes applying adhesive in a continuous open pattern having enclosed open regions free of adhesive, and wherein said open regions have an average width smaller than an average width of said pockets.

4. The method of claim 1, wherein said bonding includes bonding said fabrics using arrangements of bond points about said aggregates of SAP to produce said pockets bounded by spaced apart bond points with gaps therebetween for fluid passage.

5. The method of claim 4, wherein the arrangements of bond points form a grid characterized by lines through the bond points directed generally laterally toward side margins of the elongated absorbent core laminate at angles less that ninety degrees from a longitudinal centerline of said elongated absorbent core laminate.

6. The method of claim 1, wherein the first fabric is the bulky nonwoven.

7. The method of claim 1, wherein the second fabric is the bulky nonwoven.

8. The method of claim 1, wherein said bulky nonwoven has a thickness between 1,000 μm to 5,000 μm, a density between 0.01 g/cc and 0.08 g/cc, a basis weight between 30 g/m$^2$ and 80 g/m$^2$, and an effective pore diameter greater than 300 μm.

9. The method of claim 1, wherein at least some of said SAP is positioned between said first and second fabrics.

10. The method of claim 1, wherein the first and second fabrics are two discrete fabrics of the elongated absorbent core laminate.

11. A method of manufacturing an absorbent composite, said method comprising:
conveying a first substrate;
delivering a mixture of superabsorbent particles (SAP) with hot melt adhesive particles onto the conveyed first substrate;
as the first substrate with said mixture is conveyed, applying heat to the first substrate, thereby activating the hot melt adhesive particles and bonding the SAP with the hot melt particles and the first substrate; and
applying a second substrate atop the first substrate and SAP bonded therewith to form a pulpless absorbent composite, wherein one of said first and second substrates is a bulky non-woven, wherein said bulky non-woven is a pulpless, open, fibrous network of non-absorbent and hydrophilic fibers including fibers entangling at least some of said SAP.

12. The method of claim 11, further comprising:
bonding the first substrate with the second substrate to produce an absorbent composite laminate.

13. The method of claim 12, wherein said bonding includes using heat embossing to create a bonding pattern on the absorbent composite laminate.

14. The method of claim 11, wherein the first substrate is a bulky nonwoven material.

15. The method of claim 11, wherein said mixture comprises from 1 to 10% hot melt adhesive by weight.

16. A method of manufacturing an absorbent composite laminate for use in a disposable absorbent article, the method comprising:
conveying a first fabric into position to receive superabsorbent particles (SAP);
depositing SAP on said first fabric to provide discrete aggregates of SAP on the first fabric;
conveying a second fabric;
applying the second fabric onto said first fabric such that said discrete aggregates of SAP are positioned between said first and second fabrics to form a pulpless absorbent composite laminate; and
wherein one of said first and second fabrics is a bulky non-woven, wherein said bulky non-woven is a pulpless, open, fibrous network of non-absorbent and hydrophilic fibers including fibers entangling at least some of said SAP.

17. The method of claim 16, further comprising pockets defined between said first and second fabrics, wherein said discrete aggregates of SAP are positioned within said pockets, and said bulky non-woven includes fibers extending into said pockets and entangling at least some of said SAP within said pockets.

18. The method of claim 16, wherein said second fabric is the bulky non-woven, said bulky non-woven entangling particles in a top layer of particles of the aggregates of SAP, thereby securing, at least partly, the aggregates of SAP between the first and second fabrics.

19. The method of claim 16, wherein said first fabric is the bulky non-woven.

20. The method of claim 16, wherein said bulky nonwoven has a thickness between 1,000 μm to 5,000 μm, a density between 0.01 g/cc and 0.08 g/cc, a basis weight between 30 g/m$^2$ and 80 g/m$^2$, and an effective pore diameter greater than 300 μm.

21. The method of claim 16, wherein said aggregates of SAP are pulpless and free of an absorbent matrix.

\* \* \* \* \*

UNITED STATES PATENT AND TRADEMARK OFFICE
CERTIFICATE OF CORRECTION

PATENT NO. : 11,389,345 B2
APPLICATION NO. : 15/669714
DATED : July 19, 2022
INVENTOR(S) : Andrew C. Wright and Eugenio G. Varona It is certified that error appears in the above-identified patent and that said Letters Patent is hereby corrected as shown below:

In the Claims

Column 33, Line 56, delete "that" and insert --than--.

Signed and Sealed this
Twentieth Day of June, 2023

Katherine Kelly Vidal
*Director of the United States Patent and Trademark Office*